(12) United States Patent
Vilhelmsen et al.

(10) Patent No.: US 12,364,663 B2
(45) Date of Patent: Jul. 22, 2025

(54) METHOD AND EQUIPMENT FOR FRACTIONATION OF GRANULES FOR USE IN PHARMACEUTICAL COMPOSITIONS

(71) Applicant: Novo Nordisk A/S, Bagsvaerd (DK)

(72) Inventors: Thomas Vilhelmsen, Solroed Strand (DK); Carsten Hoeeg-Moeller, Maaloev (DK); Martin Nobert Soerensen, Koebenhavn (DK); Mette Hoeg Gaunoe, Holbaek (DK)

(73) Assignee: Novo Nordisk A/S, Bagsvaerd (DK)

( * ) Notice: Subject to any disclaimer, the term of this patent is extended or adjusted under 35 U.S.C. 154(b) by 577 days.

(21) Appl. No.: 17/639,600

(22) PCT Filed: Sep. 4, 2020

(86) PCT No.: PCT/EP2020/074750
§ 371 (c)(1),
(2) Date: Mar. 2, 2022

(87) PCT Pub. No.: WO2021/043971
PCT Pub. Date: Mar. 11, 2021

(65) Prior Publication Data
US 2022/0323360 A1    Oct. 13, 2022

(30) Foreign Application Priority Data
Sep. 6, 2019  (EP) .................................... 19195783

(51) Int. Cl.
*A61K 9/16*      (2006.01)
*A61K 31/609*    (2006.01)
(Continued)

(52) U.S. Cl.
CPC .......... *A61K 9/1682* (2013.01); *A61K 31/609* (2013.01); *B07B 1/38* (2013.01); *B07B 13/16* (2013.01); *B07B 2230/04* (2013.01)

(58) Field of Classification Search
CPC ...... A61K 9/1682; A61K 31/609; B07B 1/38; B07B 13/16; B07B 2230/04
(Continued)

(56) References Cited

U.S. PATENT DOCUMENTS 2,029,848 A * 2/1936 Wettlaufer ................ B07B 1/38
209/347
3,206,029 A * 9/1965 Hurst ........................ B07B 1/38
209/415
(Continued)

FOREIGN PATENT DOCUMENTS

CN         1720109 A   *  1/2006  ............... B07B 1/40
CN       205146673 U       4/2016
(Continued)

*Primary Examiner* — Terrell H Matthews
(74) *Attorney, Agent, or Firm* — Wesley Nicolas

(57) ABSTRACT

A sieve guide assembly and a method of fractionation using a sieve guide assembly comprising a circular sieve screen (190) and a sieve guide 310 mountable in a fractionating device, wherein the fractionating device comprises a drive adapted for: (i) in combination with a sieve screen without a sieve guide, inducing a lateral flow of granules defining lateral streamlines $31a.1$. $31b.1$, $31c.1$, $31d.1$ and an orbital flow defining orbital streamlines $31a.2$. $31b.2$, $31c.2$, $31d.2$, $31d.3$ on the sieve screen (190), and (ii) in combination with the sieve guide assembly, inducing a guided lateral flow of granules defining guided lateral streamlines (331.3) and a central guided orbital flow defining central orbital streamlines (331.2) on the sieve screen (190), whereby the sieve guide assembly is adapted to provide a uniform, controlled and effective exposure of the granules to the sieve screen.

18 Claims, 6 Drawing Sheets

(51) Int. Cl.
  *B07B 1/38* (2006.01)
  *B07B 13/16* (2006.01)
(58) Field of Classification Search
  USPC .......................................................... 209/331
  See application file for complete search history.

(56) References Cited

U.S. PATENT DOCUMENTS

| | | | |
|---|---|---|---|
| 3,932,442 | A | 1/1976 | Salmon et al. |
| 4,613,432 | A | 9/1986 | Racine et al. |
| 6,623,756 | B1 | 9/2003 | Wilber et al. |
| 10,086,047 | B2 | 10/2018 | Sauerberg et al. |
| 2011/0220745 | A1 | 9/2011 | Politi et al. |
| 2013/0327685 | A1* | 12/2013 | Kodama ................... B07B 1/38 |
| | | | 209/243 |

FOREIGN PATENT DOCUMENTS

| | | | | |
|---|---|---|---|---|
| CN | 105964535 | A | 9/2016 | |
| CN | 108883073 | A | 11/2018 | |
| FR | 1238009 | A | 8/1960 | |
| JP | 2005324170 | A | 11/2005 | |
| JP | 2016117759 | A | 6/2016 | |
| WO | 9911261 | A1 | 3/1999 | |
| WO | WO-2004050263 | A1 * | 6/2004 | ............... B07B 1/40 |
| WO | WO-2005049229 | A2 * | 6/2005 | ............... B07B 1/38 |
| WO | WO-2006092727 | A2 * | 9/2006 | ........... A61K 31/593 |
| WO | WO-2008056021 | A2 * | 5/2008 | ............... A61J 3/06 |
| WO | 2019149880 | A1 | 8/2019 | |

* cited by examiner

METHOD AND EQUIPMENT FOR FRACTIONATION OF GRANULES FOR USE IN PHARMACEUTICAL COMPOSITIONS

CROSS-REFERENCE TO RELATED APPLICATIONS

This application is a § 371 National Stage application of International Application PCT/EP2020/074750 (published as WO/2021/043971), filed Sep. 4, 2020, which claims priority to European Patent Application 19195783.6, filed Sep. 6, 2019; the contents of which are incorporated herein by reference.

The present invention relates to a sieve guide assembly comprising a sieve screen and a sieve guide mountable in a fractionating device for fractionating powders and/or granules for solid dosage forms, such as tablets, capsules, or sachets, a fractionating device for fractionating powders and/or granules for solid dosage forms, such as tablets, capsules, or sachets comprising a sieve guide assembly, a method of fractionating powders and/or granules using a fractionating device with the sieve guide assembly, a method of fractionating granules using the fractionating device comprising the sieve guide assembly.

The invention further relates to a sieve deck assembly comprising a sieve deck with the sieve guide assembly, and a sieve guide for the sieve deck.

BACKGROUND OF THE INVENTION

Powders and/or granules for the forming of solid dosage forms, such as tablets, capsules or sachets can be produced by dry granulation using a roller compactor. Powders and/or granules are used as an intermediate in the manufacturing of various solid dosage forms, such as tablets, capsules, and sachets. The powders and/or granules may be used as is or in combination with other excipients.

Fractionation can be used to improve the properties of the powders and/or granules after roller compaction. Fractionation can be accomplished by several means such as vibrational or centrifugal separation. Fractionation of the powders and/or granules by sieving is used for e.g. obtaining specific sizes and size distributions, densities, flowability, and tabletability of powders and/or granules. Such powders and/or granules may comprise a pharmaceutical active ingredient (API) or they are blended with other powders and/or granules comprising an API before e.g. tableting.

WO2008/056021 A2 relates to fractionation of a granulate for tableting which may comprise an API. The document describes that dry granulation would in many cases appear to be the best way to produce products such as tablets containing APIs, but it has been relatively little used because of the challenges in producing the desired kind of granules as well as managing the granulated material in the manufacturing process. The dry granulation methods known in the prior art produce granules that are seldom usable in a tablet manufacturing process. Conflicting process design parameters often lead to compromises where some qualities of the resulting granule product may be good, but other desirable qualities are lacking or absent. For example, the flowability characteristics of the granules may be insufficient, the non-homogeneity of the granules may cause segregation in the manufacturing process or capping in tablets, or some of the granules may exhibit excessive hardness, all of which can make the tableting process very difficult, slow and sometimes impossible. Furthermore, the bulk granules may be difficult to compress into tablets. Alternatively or additionally, the disintegration characteristics of the resulting tablets may be sub-optimal. Such problems commonly relate to the non-homogeneity and granule structure of the granulate mass produced by the compactor. For instance, the mass may have too high a percentage of fine particles or some granules produced by the compactor may be too dense for effective tableting. It is also well known in the art that in order to get uniform tablets the bulk to be tableted should be homogeneous and should have good flow characteristics. In prior art, dry granulation processes such as roller compaction, the resulting bulk is not generally homogeneously flowing, for example because of the presence of relatively large (1-3 mm) and dense granules together with very small (e.g. 1-30 micrometers) particles. This can cause segregation as the large, typically dense and/or hard granules of the prior art flow in a different way compared to the fine particles when the granulate mass is conveyed in the manufacturing process, e.g. during tableting. Because of the segregation, it is often difficult to ensure production of acceptable tablets. For this reason, in the art there are some known devices in which the small particles and sometimes also the biggest particles are separated from the rest of the granules with the help of a fractionating device such as (a set of) vibrating screen(s). According to the prior art, this process is generally complicated and noisy and the result is a relatively homogeneously flowing bulk where the granules are hard and difficult to compress into tablets. Furthermore, the process of separating small particles from granules becomes very difficult if the material is sticky and the screen-size is too small. Generally, in this process the prior art finds that the apertures of the screen must have a minimum dimension of at least 500 μm.

WO2008/056021 further describes a roller compactor in line with a fractionating device for removing fine particles and/or small granules from a granulate mass produced by a compactor. The fine particles and or small granules are carried away from the fractionating device by a carrier gas flowing in the opposite direction of the granulate mass. Accepted granules fall out of the fractioning device through a tube at the bottom of the device by effect of gravity. In another embodiment the separation is enhanced by utilizing a perforated rotating cylinder. A spiral inside the cylinder transport the granulate mass from an inlet towards an outlet of the accepted granules, a carrier gas flows in the opposite direction and ensures that only accepted granules can flow out of the outlet under the effect of gravity.

US2011/0220745 relates to fractionation of granulate mass. The document describes further aspects of a fractionating device using a carrier gas flowing in the opposite direction of a granulate mass.

U.S. Pat. No. 6,623,756 describes a method of dry granulation using a granulator 1 and screening using a screening apparatus. A fed material is compressed between two compaction rollers and subsequently dropped into a pre-break mechanism 26. The pre-break mechanism 26 breaks the compressed various sized chips into flakes which then fall into an attritor 28. The attritor subsequently further breaks up the flakes into granulate particles which fall through a screen 30. The granulated particles then fall into a screening apparatus 32, which generally contains a plurality of screens which separate out oversized as well as undersized (i.e. fines) particles. The desired sized particles are fed to product bin 36. The over- and undersized particles 38 are recycled through a feed mechanism 40.

A vibratory sieve fractionates the granules into specific sizes and size distributions by passing the granules through layers of screens with ever decreasing mesh sizes using vibration to move the granules around and through the screens. Furthermore, the vibratory sieve might require specific rotational movements of the sieve and cleaning by ultrasonication to obtain an efficient fractionation of the granules and prevent so-called blinding of the screen. Outlets exist from the different screens and yield the different fractions of granules whereof some are usable and others are under- or oversized and therefore discarded.

Vibrational sieving is a continuous process with a continuous input of material and requires an equally sized continuous output to prevent accumulation. Therefore, fractionation by vibrational sieving is a continuous process of fractionating granules into specific sizes and size distributions with specific properties as required by the next process step.

WO 2004/050263 A1 describes a sieve for removal of oversized particles for dry particulate solids and for liquids and particularly sieves in which an excitation source provides deblinding excitation of the sieve screen.

WO 2005/049229 describes and illustrates a screening apparatus provided with a upper casing and with a lower casing each one of which comprises a support structure 74 provided with a circular portion 75 and with radial portions 76 on which an upper net and a lower net rest respectively. Inside the upper casing and the lower casing, is provided a flow deflector 73, each one of which is provided with walls 79 having a preset height. Each flow deflector 73 is arranged above the net, so that the walls 79 protrude from the net, by an amount that is such that during operation the material to be screened is forced to follow a path that is longer than the path that the material to be screened would follow if the flow deflector 73 were absent. In this way, the solid particles of material remain on the net for a prolonged period in such a way that the fraction of liquid material is separated completely from the particles before the expulsion of the coarser fraction. Each flow deflector 73 comprises a further radial portion 78 and a further circular portion 77 that extends for an angle that is less than a round angle, in such a way as to define a passage gap 80. The further circular portion 77 is shaped in such a way as to couple in a joined manner with the circular portion 77, located immediately below the net. Similarly, the further radial portion 78 is shaped in such a way as to couple in a joined manner with one of the radial portions 76.

As illustrated in FIGS. 4 and 5, the radial portion 76 of the support structure 74, which is to be coupled with the radial portion 78 of the flow deflector 73, is aligned with a down stream side of an outlet opening 106, whereby the gap 80 and the outlet opening 106 is provided on opposite sides of the radial portion 78. As appears, this alignment and positioning of the gap 80 relative to the outlet 106, is provided in order to force a complete 360 degree flow path around the circular portion 77, to obtain the effect of prolonging the period which the material remains on the net.

As appears the apparatus is designed for separating liquid and solid particles by prolonging the time period on the net, which inevitably must result in increased attrition of the granules.

The efficiency of the current fractionating devices comprising a vibrational sieve are very sensitive to the feeding rate, and in some applications, it can be desired to reduce the feeding rate without compromising the quality of the product and the efficiency of the fractionating device, or simply obtaining the desired particle size distribution, flowability, density, and tabletability. Such a situation can arise when the fractionating device is operating in an in-line setup where another in-line unit determines the production rate, i.e. the feeding rate. The situation can also arise in an off-line setup where a relatively small amount is to be fractionated. In the latter case it can be desirable to prolong the production time, by reducing the feeding rate in order to avoid or reduce end effects from startup and shut-down.

SUMMARY OF THE INVENTION

It is an object of the present invention to provide further devices and methods for fractionation of granules for solid dosage forms, such as tablets, capsules, or sachets. It is a further object of the invention to provide further devices and methods for fractionation by enabling a change in the feeding rate of unfractionated granules to a fractionating device while obtaining the desired quality of the fractionated product. It is a further object of the invention to provide further devices and methods for fractionation of granules for solid dosage forms, such as tablets, capsules, or sachets, providing efficient and uniform exposure of the granules to the sieve screen.

It is a further object of the invention to provide further devices and methods for fractionation of granules comprising a salt of N-(8-(2-hydroxybenzoyl)amino)caprylic acid (also referred to as a salt of NAC herein. In one embodiment the salt of N-(8-(2-hydroxybenzoyl)amino)caprylic acid is selected from the group consisting of the sodium salt, potassium salt and/or the ammonium salt of NAC. In one embodiment the salt of N-(8-(2-hydroxybenzoyl)amino) caprylic acid is the sodium salt or the potassium salt. In one embodiment the salt of N-(8-(2-hydroxybenzoyl)amino) caprylic acid is the sodium salt sodium N-(8-(2-hydroxybenzoyl)amino)caprylate also named salcaprozate sodium and referred to as SNAC.

Salts of N-(8-(2-hydroxybenzoyl)amino)caprylic acid may be prepared using the method described in e.g. WO96/030036, WO00/046182, WO01/092206 or WO2008/028859.

It is a further object of the invention to provide further devices and methods for in-line fractionation of granules for tableting. It is a further object of the invention to provide devices and methods for roller compaction with in-line fractionation of granules for tableting.

In the present invention the inventors have solved the problem of enabling a change in the feeding rate of unfractionated granules to a conventional fractionating device comprising a sieve screen while obtaining a desirable quality of the fractionated product. The conventional fractionating device comprises a drive adapted for, in combination with the sieve screen, inducing a lateral flow of granules, i.e., a flow in the plane wherein a displacement vector comprises a component in the radial direction and in most practical instances also in a rotational or angular direction. The lateral flow is defining lateral streamlines extending in the radial direction. The streamlines also indicate and define the direction of the flow. A downstream direction is in the direction of the arrow and the flow.

The upstream direction is opposite. The fractionating device may also induce an orbital flow wherein a displacement vector comprises a component mainly in the rotational or angular direction. The orbital flow is defining orbital streamlines on the sieve screen with a rotation axis normal to the screen surface and defined at the center of the screen. For such a conventional fractionation device the feeding rate of the sieve is crucial regarding the amount of under-sized granules that will be removed by the fractionation and influences therefore directly the yield and granule properties such as particle size distribution, flowability, density, and tabletability. In addition, changes in the granule properties of the granules will change the obtainable content uniformity, mechanical strength, breaking force, friability, and the processability for the following manufacturing step of tableting, capsule filling, or sachet filling. All parameters will be negatively impacted.

In the present invention the inventors have further solved the problem of ensuring an efficient and controlled uniform exposure of granules to a sieve screen in a fractionating device.

In the disclosure of the present invention, embodiments and aspects will be described which will address one or more of the above objects or problems. Embodiments and aspects will also address objects or problems apparent from the below disclosure as well as from the description of exemplary embodiments.

In a first aspect is provided, a sieve guide assembly comprising a circular sieve screen and a sieve guide mountable in a fractionating device for fractionating granules for tableting;
wherein the fractionating device comprises a tubular rim portion for receiving the sieve guide assembly, wherein the rim portion comprises an outlet,
wherein the sieve guide is fixedly attached to the sieve screen, wherein the sieve guide comprises:
  a circular guide portion adapted to guide a central guided orbital flow, wherein the central guided orbital flow defines an orbital downstream direction, wherein the circular portion is positioned centrally on the sieve screen and thereby defining a central loading area of the sieve screen for granules to be fractionated, and wherein the circular guide portion comprises a first radial opening extending in an upstream orbital direction from a first to a second side, wherein the upstream orbital direction is opposite the downstream orbital direction,
  a lateral guide portion adapted to guide a lateral guided flow of granules from the central loading area, wherein the lateral guide portion comprises a first guide member extending in the lateral direction from the first side of the first radial opening and to a periphery of the sieve screen,
wherein the outlet of a fractionating device comprises an opening in the tubular rim portion, and wherein the opening of the outlet is extending in the upstream orbital direction from a first to a second side; and
wherein the sieve guide assembly is adapted to be mounted in a fractionating device in a specific angular position with the first lateral guide member aligned with the first side of the outlet of a fractionating device; and
whereby the lateral guided flow of granules can be guided along the first lateral guide member to the outlet, when the sieve guide assembly is mounted in the specific angular position in a fractionating device, and when the fractionating device induces an orbital and a lateral flow.

When the sieve guide is mounted in the fractionating device, the sieve guide assembly provides a uniform travel distance from the loading area to the outlet at the periphery, and minimizes or prevents a peripheral orbital flow. The guide assembly is adapted to provide a uniform and effective exposure of the granules to the sieve screen. Furthermore attrition of the granules is reduced, as a consequence of reducing or preventing the peripheral orbital flow, and by ensuring that the lateral flow is guided directly from the loading area towards the outlet. This is only possible, as the sieve guide assembly is adapted to be mounted in the fractionating device in a specific angular position with the first lateral guide member aligned with a first side of the outlet of the fractionating device.

In a further aspect, the first lateral guide member is curved. The curvature of the lateral guide member is defined by a circle positioned on the downstream side of the lateral guide member, as defined by the orbital direction, whereby the guide member is adapted to guide a curved lateral flow, i.e., a flow with both a radial and angular displacement.

In a further aspect, the sieve guide assembly further comprises a second lateral guide member extending in the lateral direction from the second side of the first radial opening, whereby the granules can be guided between the first and the second lateral guide member.

In a further aspect, the second lateral guide member is curved.

In a further aspect, the sieve guide assembly comprises a key or a key-hole adapted to ensure the assembly is mounted in the specific angular position.

In a further aspect, the sieve guide assembly is adapted to be angularly adjustable, and the sieve guide is further is adapted to be fixed or clamped at the specific angular position.

In another aspect is provided a sieve guide assembly for a fractionating device for fractionating granules, wherein the sieve guide assembly comprises:
  a circular sieve screen and a sieve guide mountable in a fractionating device for fractionating granules for tableting;
wherein the sieve guide is fixedly attached to the sieve screen, wherein the sieve guide comprises:
  a circular guide portion, wherein the circular portion is positioned centrally on the sieve screen and thereby defining a central loading area of the sieve screen for granules to be fractionated, and wherein the circular guide portion comprises a first radial opening extending from a first to a second side,
  a lateral guide portion comprising a first lateral guide member extending from the first side of the first radial opening and to a periphery of the sieve screen, and a second lateral guide member extending from the second side of the first radial opening and towards the periphery,
whereby the lateral guided flow of granules can be guided along the first and second lateral guide members and directly towards an outlet, when the sieve guide assembly is mounted in a fractionating device, and when the fractionating device induces an orbital and a lateral flow.

In another aspect of the invention is provided a sieve guide assembly comprising a circular sieve screen and a sieve guide mountable in a fractionating device for fractionating granules for solid dosage forms, such as tablets, capsules or sachets, wherein the fractionating device comprises a drive adapted for: (i) in combination with a sieve screen without a sieve guide, inducing a lateral flow of granules defining lateral streamlines and an orbital flow defining orbital streamlines on the sieve screen, and (ii) in combination with the sieve guide assembly, inducing a guided lateral flow of granules defining guided lateral streamlines and a central guided orbital flow defining central orbital streamlines on the sieve screen;
wherein the sieve guide is fixedly attached to the sieve screen, wherein the sieve guide comprises:
  a circular guide portion adapted to guide the central guided orbital flow, wherein the circular portion is positioned centrally on the sieve screen and thereby defining a central loading area of the sieve screen for granules to be fractionated, and wherein the circular guide portion comprises a first radial opening, a lateral guide portion adapted to guide the guided lateral flow of granules from the central loading area, comprising a first and a second lateral guide member extending from each side of the first radial opening and to a periphery of the sieve screen, wherein the lateral guide members define a second radial opening at the periphery, whereby the lateral guide members define a lateral flow path with an inlet at the first radial opening and an outlet at the second radial opening, and thereby ensuring a uniform travel distance from the loading area to the outlet at the second radial opening; and whereby the guide assembly is adapted to provide a controlled uniform and effective exposure of the granules to the sieve screen.

Hereby is provided a sieve guide which eliminates excessive attrition of the granules.

In a further aspect, the first and the second lateral guide members are curved, and wherein the shape of the curved guide members are adapted to the guided lateral streamlines to provide a uniform thickness of a layer of the guided lateral flow of granules.

In a further aspect, the sieve guide circumference's an area of the sieve screen defining a primary sieving area comprising the central loading area and the lateral flow path, wherein the remaining area of the sieve screen defines a secondary sieving area, and whereby less than 20% of the granules will be exposed to the sieve screen at the secondary sieving area.

In a further aspect, the central orbital flow defines a direction of motion, wherein the first lateral guide member is positioned in the direction of motion relative to the second lateral guide member, wherein the second lateral guide member comprises an opening at the periphery of the sieve screen adapted to allow granules escaping the sieve guide and following a peripheral orbital flow defining a peripheral orbital streamline to enter the lateral flow path through the opening in the second guide member.

In a further aspect, the central orbital flow defines a direction of motion, wherein the first radial opening is positioned at a first angular position and the second radial opening is positioned at a second angular position, wherein the second angular position is in the direction of motion relative to the first angular position, whereby the lateral flow path from the central loading area is curved.

In a further aspect, an arch length defined by the second radial opening and a center of the sieve screen defines a circular sector with an angle smaller than 70 degrees, wherein granules can flow from the first radial opening to the second radial opening to define one or more guided lateral streamlines of the guided lateral streamlines, completely within the area defined by the circular sector.

In a further aspect, an arch length defined by the second radial opening and a center of the sieve screen defines a circular sector with an angle between 40 and 60 degrees, wherein granules can flow from the first radial opening to the second radial opening to define one or more guided lateral streamlines of the guided lateral streamlines, completely within the area defined by the circular sector.

In a further aspect, the central loading area and the lateral flow path define a primary sieving area, which is the fraction of the total possible area of the sieve screen, and wherein the fraction is in the range of 10-30%.

In another aspect is provided, a fractionating device for fractionating granules for solid dosage forms, such as tablets, capsules, or sachets, wherein the fractionating device comprises a sieve guide assembly as described herein, wherein the fractionating device comprises a tubular rim portion for receiving the sieve guide assembly, wherein the rim portion comprises an outlet, wherein the outlet (132) of the fractionating device is provided as an opening in the tubular rim portion extending in the upstream orbital direction from a first to a second side.

In another aspect is provided a fractionating device for fractionating granules, wherein the fractionating device comprises:

a sieve deck with an inlet and a tubular rim portion comprising an outlet, a sieve screen and a sieve guide received in the sieve deck, wherein the sieve guide is fixedly attached to the sieve screen, and wherein the sieve guide comprises:

a circular guide portion, wherein the circular portion is positioned centrally on the sieve screen and thereby defining a central loading area of the sieve screen adapted for receiving granules received through the inlet, wherein the circular guide portion comprises a first radial opening extending from a first to a second side, a lateral guide portion comprising a first guide member extending from the first side of the first radial opening and to a periphery of the sieve screen, wherein the outlet of the sieve deck comprises an opening extending from a first to a second side; and wherein the sieve guide is arranged in a specific angular position with the first lateral guide member aligned with the first side of the outlet of the sieve deck, wherein the first radial opening is arranged with an angular overlap with the outlet, whereby the granules can be guided along the first lateral guide member and directly to the outlet, when the fractionating device induces an orbital and a lateral flow.

Hereby are the granules guided directly to the outlet from the loading area, and attrition of the granules can be reduced.

In a further aspect, the first lateral guide member is curved.

In a further aspect, the fractionating device further comprises a second lateral guide member extending in the lateral direction from the second side of the first radial opening.

In another aspect is provided a fractionating device for fractionating granules for tableting, wherein the fractionating device comprises a sieve guide assembly as described above, and a drive adapted for, in combination with the sieve guide assembly, inducing a guided lateral flow of granules defining guided lateral streamlines and a central guided orbital flow defining central orbital streamlines on the sieve screen.

In a further aspect, the fractionating device further comprises a sieve deck, wherein the sieve deck comprises a tubular deck portion comprising a rim, wherein the tubular portion comprises a first end defining an inlet and a second end adapted for assembly with the sieve screen, wherein the rim comprises an opening defining an outlet, and wherein the inlet enables loading of granules onto the central loading area of the sieve screen. The outlet is aligned with the second radial opening and thereby enables fractionated granules to exit.

In a further aspect, the rim supports a peripheral orbital flow for granules escaping the sieve guide defining a peripheral orbital streamline and a direction of motion, wherein the first lateral guide member is positioned in the direction of motion relative to the second lateral guide member, wherein the second lateral guide member comprises an opening at the periphery of the sieve screen adapted to allow granules escaping the sieve guide and following the peripheral orbital flow to enter the lateral flow path through the opening in the second guide member.

In a further aspect, the fractionating device comprises a sieve guide assembly as described above, and a drive adapted for: (i) in combination with a sieve screen without a sieve guide, inducing a lateral flow of granules defining lateral streamlines and an orbital flow defining orbital streamlines on the sieve screen, and (ii) in combination with the sieve guide assembly, inducing a guided lateral flow of granules defining guided lateral streamlines and a central guided orbital flow defining central orbital streamlines on the sieve screen.

In a further aspect, the fractionating device further comprises a vibrator arranged to vibrate and deblind the sieve screen.

In another aspect is provide, a method of fractionating granules for solid dosage forms, such as tablets, capsules, or sachets comprising fractionating granules using a fractionation device as described herein.

In a further aspect the method of fractionating granules for solid dosage forms, such as tablets, capsules, or sachets, using the fractionating device as described herein, the method comprises fractionating the granules, uniformly exposing the granules to the sieve screen and guiding them directly to the outlet (132) from the central loading area.

In another aspect is provide, a method of fractionating granules for solid dosage forms, such as tablets, capsules, or sachets comprising
a) loading the granules to be fractionated onto the central loading area of the screen of a fractionating device as described herein,
b) fractionating the granules and
c) collecting the fractionated granules at the outlet.

In another aspect is provided a method of fractionating granules for tableting using the fractionating described herein, wherein the method comprises fractionating the granules and uniformly exposing the granules to the sieve screen.

In another aspect is provided a method of fractionating granules comprising SNAC using the fractionating as described herein, wherein the method comprises fractionating the granules comprising SNAC and uniformly exposing the granules to the sieve screen.

In a further aspect the method further comprises guiding the granules along the lateral flow path in a layer of uniform thickness.

In a further aspect the method further comprises continuously fractionation of granules.

In a further aspect the method further comprises fractionating granules in an in-line-setup.

In a further aspect the method further comprises providing a roller compactor in-line with the fractionating device, whereby the roller compactor is feeding unfractionated granules into the fractionating device.

In a further aspect the roller compactor feeds directly into the fractionating device, whereby there is no accumulation and a steady state feed rate to the fractionating device.

In a further aspect the method further comprises exposing a major portion of the granules to the sieve screen at a primary sieving area comprising the central loading area and the lateral flow path, wherein the major portion of the granules comprises more than 80% of the total amount of unfractionated granules.

In a further aspect the method further comprises exposing a minor portion of the granules to the sieve screen at a secondary sieving area comprising the area of the sieve screen not being the central loading area and not being the area of lateral flow path, wherein the minor portion comprises less than 20% of the total amount of unfractionated granules.

In another aspect is provided a sieve deck assembly comprising a sieve deck comprising a tubular deck portion comprising a rim, wherein the tubular portion comprises a first end defining an inlet and a second end adapted for assembly with the sieve screen and the sieve screen frame, wherein the rim comprises an opening defining an outlet; a sieve guide assembly as described above.

In another aspect is provided a sieve guide for a sieve deck assembly mountable in a fractionating device for fractionating granules for tableting, wherein the fractionating device comprises a sieve screen, and a drive adapted for: (i) in combination with the sieve screen without a sieve guide, inducing a lateral flow of granules defining lateral streamlines and an orbital flow defining orbital streamlines on the sieve screen, and (ii) in combination with the sieve guide and the sieve screen, inducing a guided lateral flow of granules defining guided lateral streamlines and a central guided orbital flow defining central orbital streamlines on the sieve screen;

wherein the sieve deck assembly further comprises a sieve deck and a sieve screen frame supporting the sieve screen;

wherein the sieve deck comprises a tubular deck portion comprising a rim, wherein the tubular portion comprises a first end defining an inlet and a second end adapted for assembly with the sieve screen and the sieve screen frame, wherein the rim comprises an opening defining an outlet; and wherein, for the sieve deck assembly in an assembled state, the sieve deck is assembled with the sieve screen frame and the sieve screen, whereby:
the inlet enables loading of granules onto a central loading area of the sieve screen,
the outlet enables a fraction of the loaded granules to flow out of the sieve deck assembly;
wherein the sieve guide comprises a circular portion, wherein the sieve guide is adapted to be fixedly attached to the sieve screen and whereby the circular portion defines the central loading area;
wherein the circular portion is adapted to guide the central guided orbital flow, wherein the circular portion further comprises an opening for guiding granules from the central orbital flow to the lateral guided flow;
wherein the sieve guide further comprises a lateral portion extending from the opening of the circular portion to the outlet, wherein the lateral portion is adapted for guiding the granules along the guided lateral flow,
wherein the lateral portion is adapted to follow the streamlines of the guided lateral flow, whereby it is ensured that the granules can flow in a layer with a uniform thickness from the central portion and to the outlet.

In a further aspect the invention provides compositions comprising granules of a salt of N-(8-(2-hydroxybenzoyl)amino)caprylic acid (NAC), such as SNAC.

The size distribution of the granules of the salt of NAC in the composition may vary. In one embodiment the composition comprising granules has been fractionated using sieves providing a cut of 90 µm to remove smaller particles. It is noticed that a composition so obtained may still include granules smaller than 90 µm, although the amount (% w/w) of such is decreased by the fractionation.

In one embodiment the composition has more than 5% w/w of granules smaller than (<) 90 µm. In one embodiment the composition has 8-20% w/w of granules smaller than (<) 90 µm or such as 8-18, 9-15 or such as 9-12% w/w smaller than (<) 90 µm.

In one embodiment the composition comprising granules of a salt of N-(8-(2-hydroxybenzoyl)amino)caprylic acid has more than 5% w/w of granules smaller than (<) 90 µm. In one embodiment the composition comprising granules of a salt of N-(8-(2-hydroxybenzoyl)amino)caprylic acid has 8-20% w/w of granules smaller than (<) 90 µm or such as 8-18, 9-15 or such as 9-12% w/w smaller than (<) 90 µm.

The processability of a composition of granules may further vary depending on the characteristics of the composition. Such a characteristic may be flowability, and more specifically funnel flowability, which may be measured as described in Example 4 herein.

In one embodiment the composition has a funnel flowability below 50 g/s, such as 5-40 g/s, such as 10-35 g/s, such as 5-30 g/s or such as 15-25 g/s.

In one embodiment the composition comprising granules of a salt of N-(8-(2-hydroxybenzoyl)amino)caprylic acid has a funnel flowability below (<) 50 g/s, such as a funnel flowability of 5-30 g/s.

The processability of a composition of granules may further vary depending on the principal component 1 which may be measured as described in Example 5 herein.

In one embodiment the composition comprising granules has a score for principal component 1 (PC1) below 0.

In one embodiment the composition comprising granules has a score for principal component 1 (PC1) of −2 to 0, such as −2 to −0.5, such a −2 to −0.7.

In one embodiment the composition comprising granules a salt of N-(8-(2-hydroxybenzoyl)amino)caprylic acid has a score for principal component 1 (PC1) below 0.

In one embodiment the composition comprising granules a salt of N-(8-(2-hydroxybenzoyl)amino)caprylic acid has a score for principal component 1 (PC1) of −2 to 0, such as −2 to −0.5, such a −2 to −0.7.

In one embodiment the composition comprising granules has a bulk density of more than (>) 0.51 g/mL.

The processability of a composition of granules may further vary depending on the compressibility which may be measured as described in Example 3 herein.

In one embodiment the composition comprising granules has a compressibility of more than (>) 15%.

In one embodiment the composition comprising granules of a salt of N-(8-(2-hydroxybenzoyl)amino)caprylic acid has a compressibility of more than (>) 15%.

In one embodiment the composition comprising granules of a salt of N-(8-(2-hydroxybenzoyl)amino)caprylic acid has a bulk density of more than (>) 0.51 g/mL.

In further embodiments the composition has
a) 8-20% w/w of granules smaller than (<) 90 µm, such as 8-18, 9-15 or such as 9-12% w/w,
b) has a compressibility above 15%,
c) has a funnel flowability below 50 g/s, such as between 5-40 g/s, 8-30 g/s, 5-30 g/s, 10-20 g/s or such as between 12-18 g/s or/and
d) has a score below 0 for principal component 1, such as a PC1 score of −2 to 0, such as −2 to −0.5, such a −2 to −0.7.

Such composition may according to the invention comprise further pharmaceutical excipients.

In one embodiment the granules of a salt of N-(8-(2-hydroxybenzoyl)amino)caprylic acid further comprise a lubricant, such as magnesium stearate. In one embodiment the granules comprising a salt of N-(8-(2-hydroxybenzoyl)amino)caprylic acid further comprise a filler, such as microcrystalline cellulose. In one embodiment the granules comprises a salt of N-(8-(2-hydroxybenzoyl)amino)caprylic acid, a lubricant such as magnesium stearate and a filler such as microcrystalline cellulose (MCC).

Such granule composition may according to the invention comprise a pharmaceutical active ingredient. Alternatively, a pharmaceutical active ingredient may be included in the solid dosage form at any time in the production of a solid dosage form comprising such granule composition.

In another aspect is provided a method of producing a solid dosage form, such as tablets, capsules, or sachets comprising:
a) obtaining granules comprising a salt of N-(8-(2-hydroxybenzoyl)amino)caprylic acid (NAC),
b) fractionating said granules using a fractionation device as described herein and
c) preparing said solid dosage form using the fractionated granules.

In a further aspect the fractionated granules are a composition comprising granules as described above.

In another aspect the method of producing a solid dosage form, such as tablets, capsules, or sachets, the solid dosage form comprises one or more pharmaceutical active ingredient(s) and optionally one or more further pharmaceutically acceptable excipient(s).

BRIEF DESCRIPTION OF THE DRAWINGS

In the following, embodiments of the invention will be described with reference to the drawings.

Figure 1:
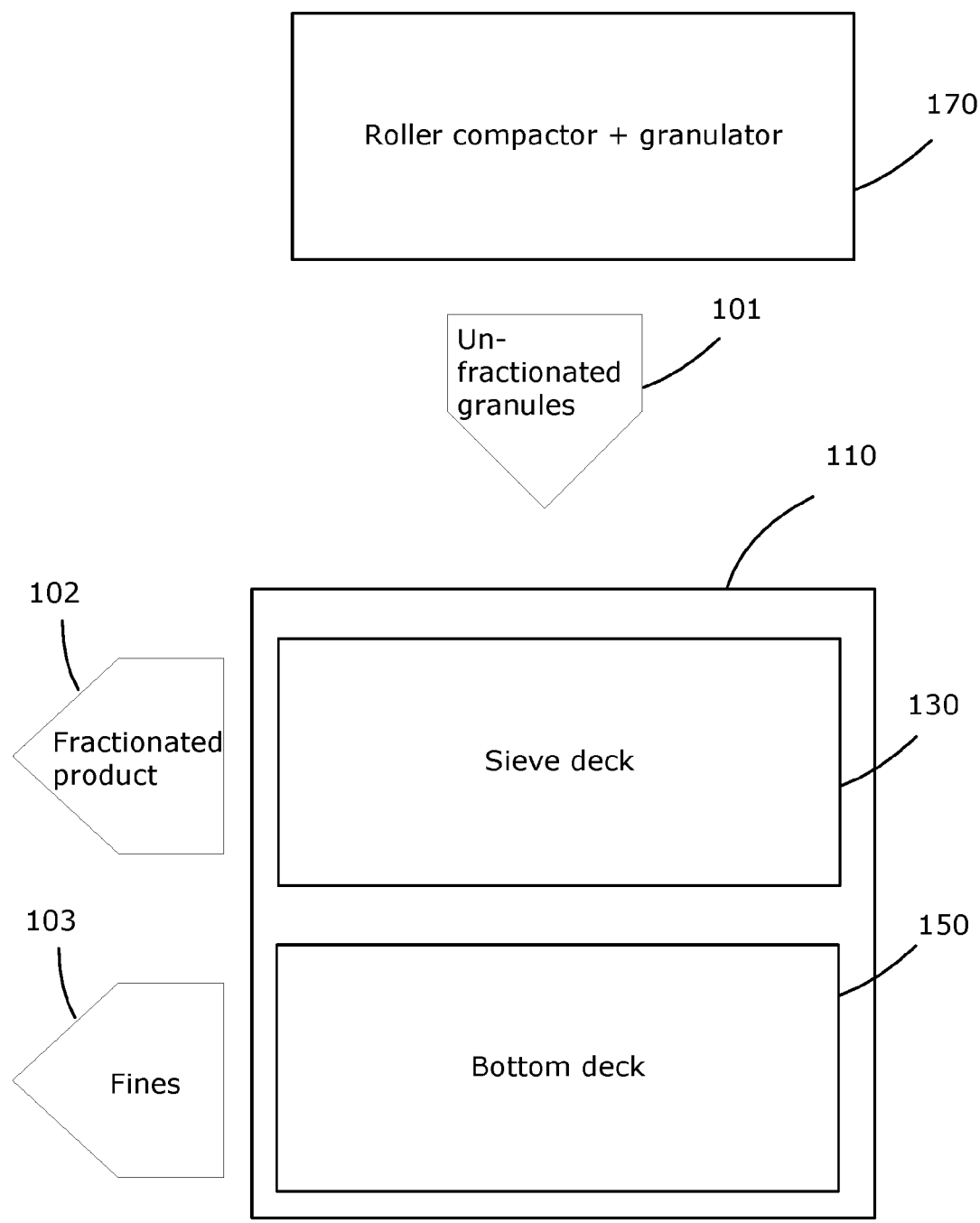
FIG. 1 schematically illustrates an in-line setup of the fractionating device 110. A roller compactor 170 providing unfractionated granules for tableting is arranged above the fractionating device 110, whereby the granules can flow by gravity to the fractionating device.

In the figures like structures are mainly identified by like reference numerals. Numbers e.g. 200, 201, 202 are used to denote features on the drawing. Numbers combined with letters e.g. 212a, 212b are used to denote features with a similar function, and these features can be referred to individually as 212a and 212b or in common as 212. Further details of a feature can be denoted by a number followed by a dot and a running number of 1 or 2 digits.

DESCRIPTION OF EXEMPLARY EMBODIMENTS

When in the following terms such as "upper" and "lower", "right" and "left", "horizontal" and "vertical" or similar relative expressions are used, these only refer to the appended figures and not necessarily to an actual situation of use. The shown figures are schematic representations for which reason the configuration of the different structures as well as their relative dimensions are intended to serve illustrative purposes only. When the term member is used for a given component it can be used to define a unitary component or a portion of a component, having one or more functions.

In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

As used herein, the term "continuous period" is used to describe a period without interruption or uninterrupted extension. A "continuous method" is used to describe a method which can be continued without interruption due to external conditions determined by the nature of the process, e.g., the process is stopped due to required cleaning of the equipment or the process is stopped due to excessive accumulation which blocks the process or prevents the functioning of the equipment.

As used herein, the term "granules" refers broadly to pharmaceutical ingredients in any form, such as powders, particles, granules and aggregates which are used in the preparation of solid dose formulations. The set-up described herein fractionates granules obtained by dry granulation but is apparent that fractionations may be applied to pharmaceutical ingredients in any form where a fractionation is required prior to the preparation of a solid dose formulation.

FIG. 1 schematically illustrates an in-line setup of the fractionating device 110. A roller compactor 170 with granulator e.g. roller compacted unfractionated granules for tableting is arranged above the fractionating device 110, whereby the granules can flow by gravity to the fractionating device. Valve means can be used to regulate the rate of feeding granules into the fractionating device 110. In a continuous in-line process, the maximum feeding rate will be the production rate of unfractionated granules by the roller compactor.

Figure 2A:
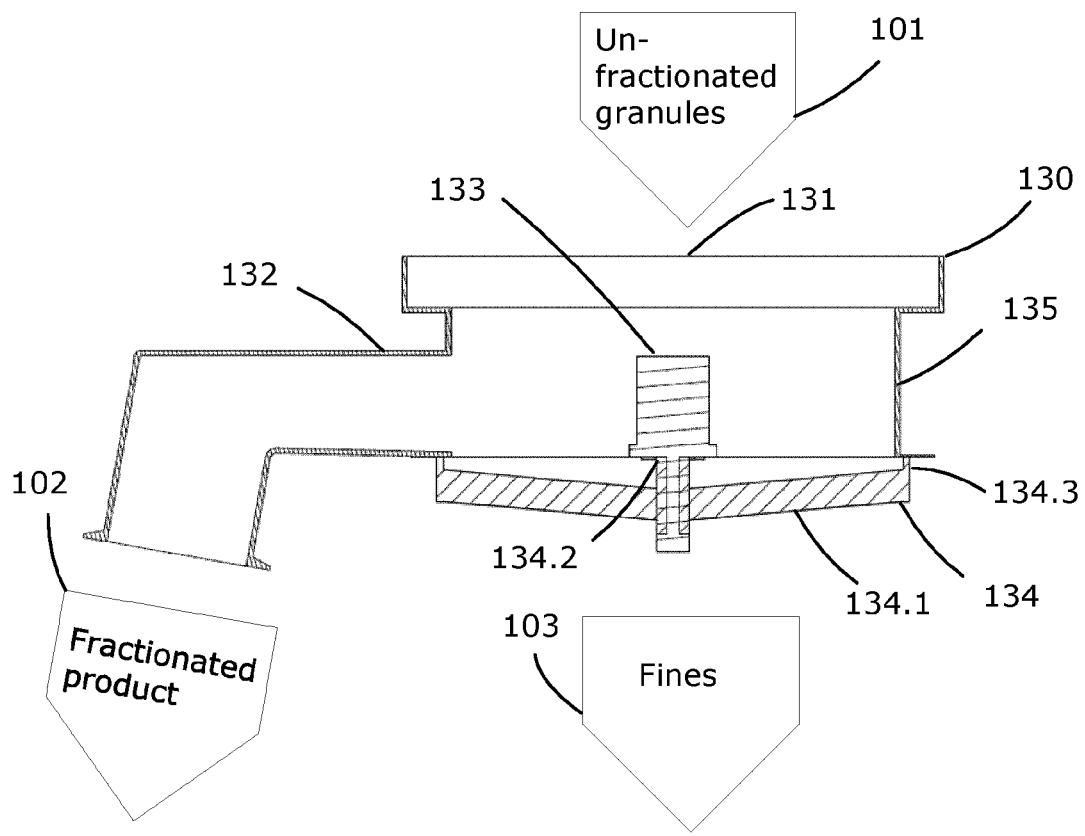
FIG. 2A illustrates the conventional sieve deck 130 seen in a profile cross-section.

FIG. 2A illustrates the conventional sieve deck 130 seen in a profile cross-section seen from above. Unfractionated granules are loaded through an inlet 131 to a central portion of the sieve deck and exits through an outlet 132 from the sieve deck. The loading can be centralized using a funnel shaped inlet chute or a lid with an integral inlet chute (not shown on figure). On the figure is also shown an ultra-sonic probe 133 to deblind a sieve screen (not shown) during fractionation, as granules otherwise tend to blind or block the apertures. A sieve frame 134 is adapted to span over the width of the sieve deck 130 and is adapted to support a sieve screen. The sieve frame comprises beams 134.1 connecting a central portion 134.2 and a rim portion 134.3. The central portion of the sieve frame 134 can be connected to the ultra-sonic probe 133 to transfer vibrations through the frame and a supported sieve screen. The sieve deck 130 comprises a rim 135 which circumference's granules on a sieve screen. The rim forms a tubular portion resembling a cylindar. Flow of unfractionated granules is indicated with block arrow 101, flow of fines to the bottom deck (bottom deck not shown) with block arrow 103, and flow of fractionated product with block arrow 102.

Figure 2B:
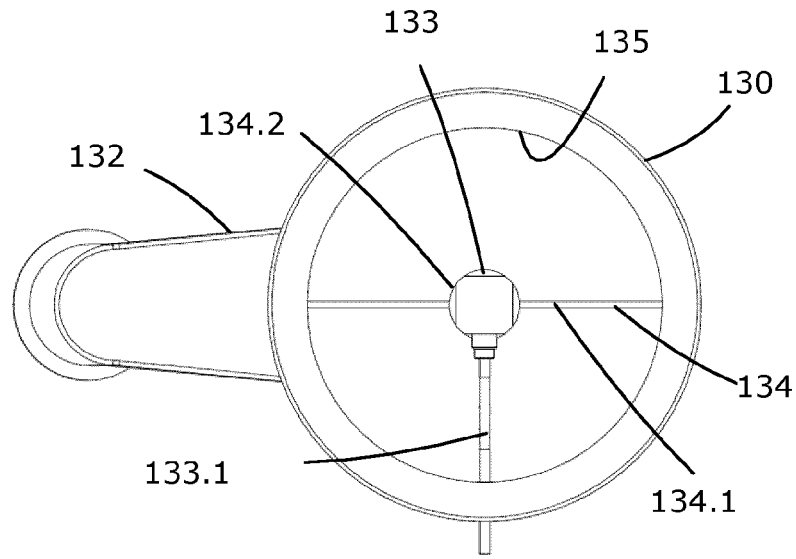
FIG. 2B illustrates the conventional sieve deck 130 of FIG. 2A in a bird perspective.

FIG. 2B illustrates the conventional sieve deck 130 of FIG. 2A in a bird perspective, i.e., seen from above. The frame 134 is illustrated as beams 134.1 extending from the central support portion 134.2 towards the rim portion 134.3. Even though the figure only illustrates two beams 134.1, in some embodiments a frame may comprise more than two beams distributed symmetrically around the central portion 134.2, e.g., four beams symmetrically distributed. The sieve screen is not shown on the figure. The ultrasonic probe 133 includes a cable 133.1.

According to an embodiment of the current disclosure, a conventional fractionating device as described in FIGS. 1 and 2 was used in combination with a conventional sieve screen. The apertures in the sieve screen is usually specified in micrometer (µm).

In some embodiments the measure of the aperture is the smallest dimension of the aperture, and in other embodiments the measure is the diameter of an inscribed circle of the diameter. In one embodiment a sieve screen in the range 50-250, 55-180, 60-150 or 70-125 µm can be used, and in other embodiments a sieve screen in the range 80-100 µm can be used. In an experiment according to the present disclosure with a conventional 90 µm sieve screen in an in-line setup as illustrated in FIG. 1, it was found that, at the production rate given by the roller compactor, the vibrational sieve removed an unacceptably high amount of undersized granules and particles by the fractionation and resulted thus in an unacceptably low yield of 65% fractionated product as 26% was lost to undersized granules (Table 1).

The high loss to undersized granules from the 90 µm sieve screen, is a consequence of an overly efficient exposure to the sieve mesh and thus a too efficient fractionation at the given production rate as dictated by the roller compactor. In addition, the too efficient exposure introduces or increases attrition of the granules, which amplifies the negative consequences and thus the low yield.

In addition, the high amounts removed of undersized granules and particles also resulted in a low amount of small granules and particles in the fractionated product causing the flowability to be overly high and the compressibility too small (Table 2.1, Table 2.2, Table 3 and Table 4). The relevant properties of the granules for the purpose of tableting comprise especially content uniformity, mechanical strength, breaking force, friability, and the processability, which can be negatively impacted by changes in the particle size, flowability, and compressibility of the fractionated granules (Table 6). Furthermore, if a continuous flow through the vibrational sieve is prevented then these negative impacts will be even higher as unacceptably high amounts of under-sized granules and particles will exit through the outlet of the sieve deck 130 for larger sized particles. Consequently, the properties of the final tablet will be affected by the production rate of the roller compactor when placing the conventional fractionating device in-line with the roller compactor.

Figure 3A:
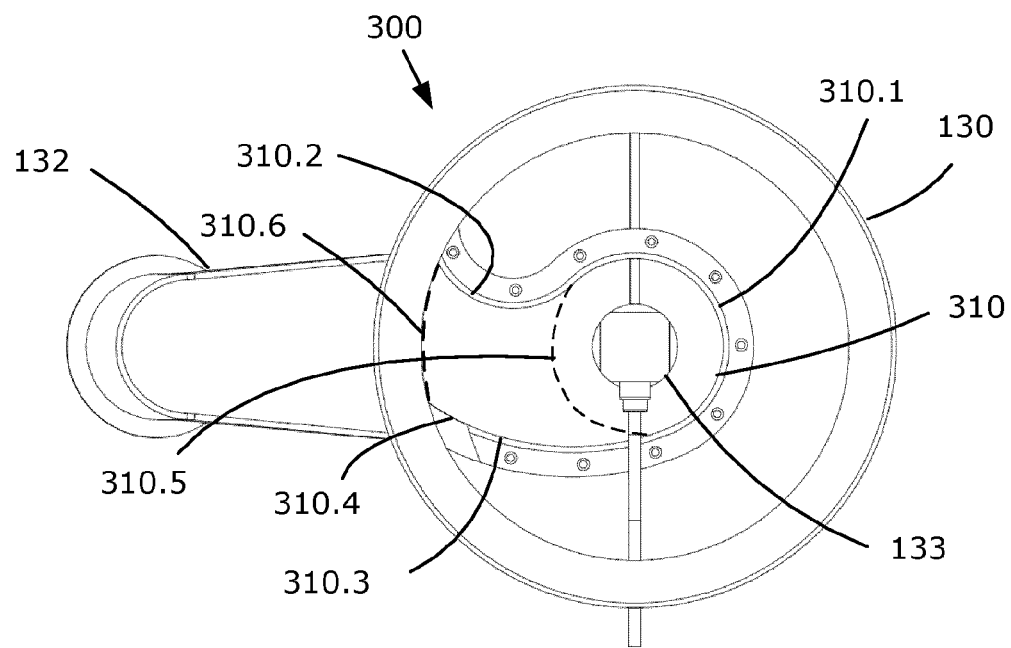
FIGS. 3A, 3B, and 3C shows an exemplary embodiment of a sieve guide 310 according to the present disclosure.
Figure 3B:
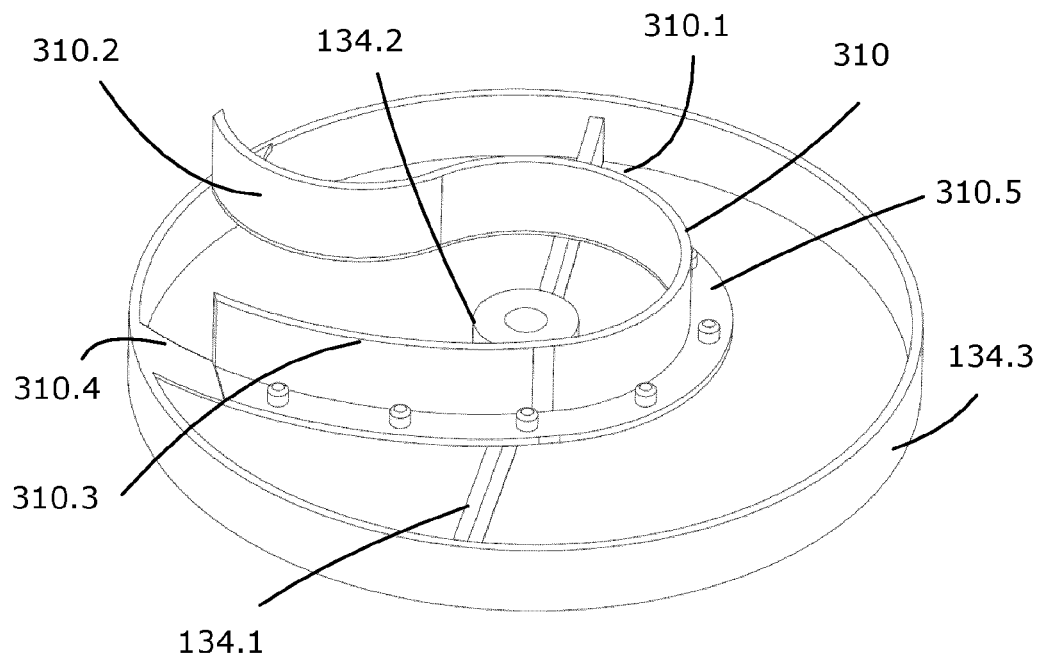
Figure 3C:
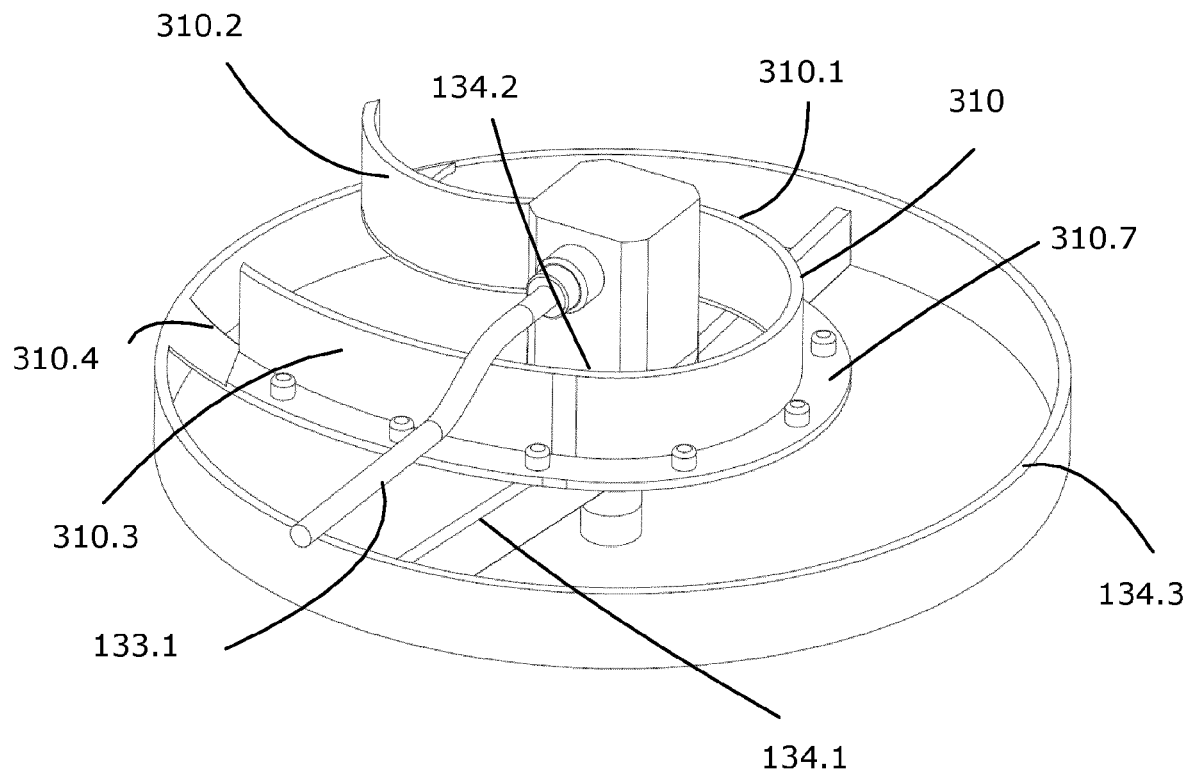
Figure 3D:
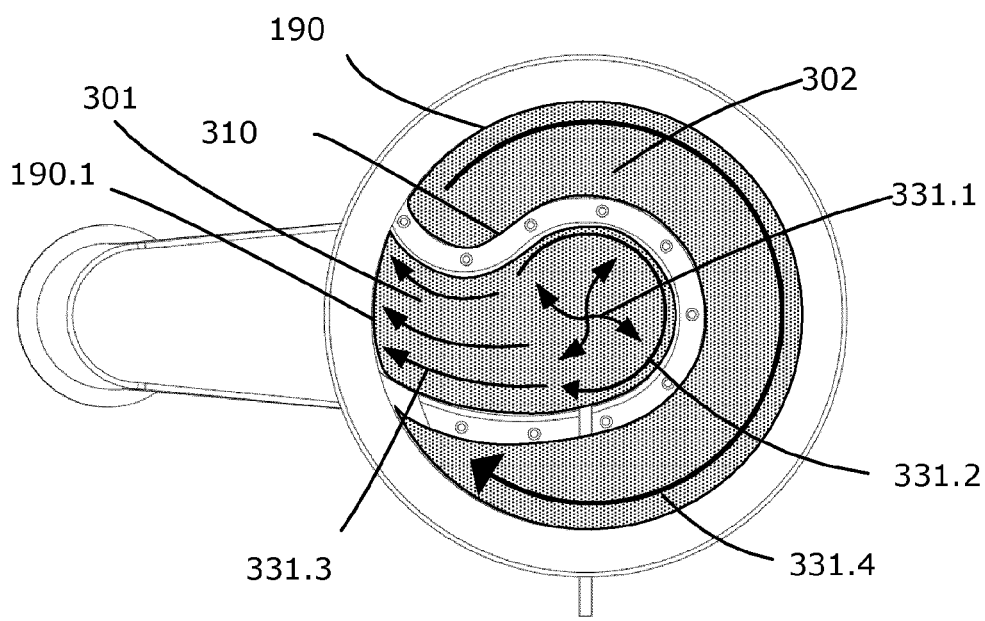
FIG. 3D schematically shows the working principles of the sieve guide 310 fixedly attached to the sieve screen 190.

FIGS. 3A, 3B, 3C, 3D and 3E shows an exemplary embodiment of a sieve guide 310 according to the present disclosure. The sieve guide 310 for a vibrational sieve ensures efficient exposure to the sieve mesh and simultaneously an efficient transport of the granules across the sieving mesh directly towards the outlet 132 from the sieve. The illustrated sieve guide comprises a circular portion 310.1 defining the loading portion of a supported sieve, i.e., the sieve screen is to be supported between the support beams 134.1 and the sieve guide 310. The circular portion is adapted to guide an orbital flow during fractionation. Furthermore, the circular portion comprises an opening towards an outlet of the sieve deck, and thereby guides the flow in a lateral direction. The illustrated sieve guide further comprises a lateral portion 310.2, 310.3 for further guiding the lateral flow. The lateral portion comprises a first lateral member 310.2 and a second lateral member 310.3. The first lateral member 310.2 extends from the circular portion 310.1 to the rim 134.3 of the sieve frame 134, or to the periphery of a supported sieve screen 190 (see FIG. 3D). The first lateral member 310.2 is curved to follow streamlines of the lateral flow. The second lateral member 310.3 extends from the circular portion towards the rim 134.3. However, a small gap 310.4 is provided between the end and the rim 134.3. When the frame 134 and the sieve guide 310 are mounted in a sieve deck 130, the first lateral guide member 310.2 extends to the rim 134.3, at a position adjacent to the outlet to allow a guided lateral flow of granules entering through the first radial opening and flowing continuously along the first lateral guide member 310.2, to exit through the outlet and thereby minimizing a peripheral orbital flow at the periphery of the sieve screen 190. For the second lateral guide member 310.3, a small gap 310.4 is provided between the end of the second lateral guide member 310.3 and the rim 134.3, or periphery of the sieve screen 190, to allow granules escaping the sieve guide, and starting to orbit at the periphery, to enter through the gap 310.4 and exit through the outlet 132. The sieve guide 310 comprises a flange 310.7 to be attached to the screen. The attachment can be provided by welding and/or bolts and nuts. As illustrated in FIG. 3D, the sieve guide 310 defines a primary sieving area 301 and a secondary sieving area 302. If granules escape the primary sieving area 301, they will re-enter through the gap 310.4 due to induction of a clockwise orbital flow as illustrated in FIG. 3D, and described later in the description. If an induced orbital flow is counter clockwise the design of the sieve guide should be inverted accordingly.

As seen in the Examples (Table 1), the yield of the fractionated product increased markedly to an acceptable 84% of fractionated product as only 9% was lost to undersized granules with the use of the sieve guide. The improved yield of fractionated product is due to the asymmetrical placement of the sieve guide that guides the granules directly from the loading area defined by the circular portion directly towards the outlet 132 along the first lateral guide member 310.2. Hereby is provided an efficient and controlled uniform transport as opposed to the sieve without the sieve guide where granules are scattered all over the sieve, and wherein a major portion may orbit at the periphery of the sieve screen. The sieve guide provides a direct flow from the loading area to the periphery 190.1 and thereby the outlet 132, when the sieve guide is mounted in the fractionating device. Hence, the reduction of the effective sieving area and the short uniform travel distance to the outlet for all the granules makes the sieve with the sieve guide superior.

In addition, the particle size distribution only shifts slightly when using the sieve guide as it only results in slightly more fine particles (<90 μm) and slightly fewer large particles (>355 μm) (Table 2.1, table 2.2) despite the markedly increase in yield. Hence, this shows that the guiding of the granules directly towards the outlet from the sieve by the sieve guide prevents excessive attrition of the granules during sieving and thus increases the yield. Furthermore, the use of the sieve guide increases the bulk and tap densities and the compressibility (table 3) enabling a more efficient storage, transport, and tabletability due to the reduced volume of the bulk. The flowability is also improved using the sieve guide as it reduced the flowability to around 15 g/s (Table 4) and thus preventing poor content uniformity in tablets due to the flowability no longer being overly free flowing and prone to segregation as for the sieving without guide. These differences in the physical properties of the fractionated product when using a sieve guide is further shown based on the significantly different near infra-red spectra (Table 5). Finally, the properties of the fractionated product also have beneficial effects on the mechanical strength of tablets (Table 6).

Consequently, the highest yields are obtained using the sieve guide 310 (Table 1), while it is ensured that the fractionated granules comprise improved properties with respect to flowability, density, particle sizes and size distributions, and processability. The implementation of a continuous manufacturing of granules with in-line fractionation has therefore a tremendous impact on the capacity of the manufacturing facilities as it almost halves the time and resource requirements for manufacturing granules. The sieve guide according to the present disclosure is therefore of paramount importance for the success of this achievement.

FIGS. 3A and 3D schematically shows the working principles of the sieve guide 310 fixedly attached to the sieve screen 190. The central circular portion 310.1 of the sieve guide 310 defines an area for loading unfractionated granules the loaded granules are laterally dispersed, which is indicated by lateral streamlines 331.1. The central portion is adapted to support a central guided orbital flow, indicated with a streamline 331.2. As the central portion comprises a first radial opening 310.5, i.e., an opening in the radial direction, the granules following the central orbital flow are guided onto the lateral flow path, guided by the lateral guiding portion of the sieve guide 310, and out through the second radial opening 310.6 (opening in the radial direction). The area of the sieve screen comprising the central loading area and the lateral flow path is defined as the primary sieving area 301, wherein the majority of the unfractionated granules are exposed only to this area. Some granules may escape the primary area defined by the sieve guide and enters a secondary sieving area 302 defined between an outer surface of the sieve guide and the periphery 190.1 of the sieve screen. The rim 135 of the sieve deck 130 is adapted to support a peripheral orbital flow, which is indicated by streamline 331.4. Granules escaping the sieve guide will enter the secondary sieving area and move laterally towards the periphery (not indicated on figure), at the periphery they will start to orbit and enter into the primary sieving area 301, through a peripherally positioned opening 310.4 in the lateral guide portion, more particularly between the end of the second lateral guide member 310.3 and the rim of the fractionating device.

Figure 3E:
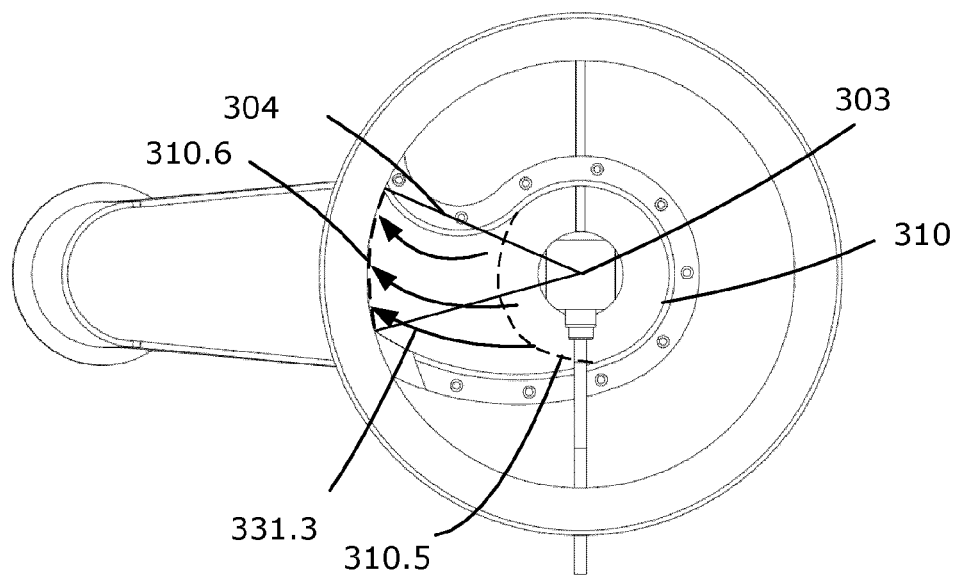
FIG. 3E illustrates a circular sector 304 defined by the radial outlet opening 310.6 and the center 303 of the circular sieve screen 190.

FIG. 3E illustrates a circular sector 304 defined by the radial outlet opening 310.6 and the center 303 of the circular sieve screen 190. The circular sector 304 is a measure of the degree of asymmetric arrangement of the lateral flow path and defines an angular portion of the periphery of the screen which is to be aligned with the outlet 132 of the sieve deck 130. The flow path does not rotate or spiral around the center, and the entire lateral flow path is positioned at one side of the center. The granules can travel from the central loading portion to the outlet 132 through the second opening 310.6 within the area defined by the circular sector, and the granules cannot reach the outlet 132 without entering the area of the circular sector. Granules flowing from first radial opening 310.5 guided by the first lateral guide member 310.2 to the second radial opening 310.6 define one or more guided lateral streamlines 331.3, completely within the area defined by the circular sector 304, and none of the guided lateral streamlines are completely outside the area.

Figure 4A:
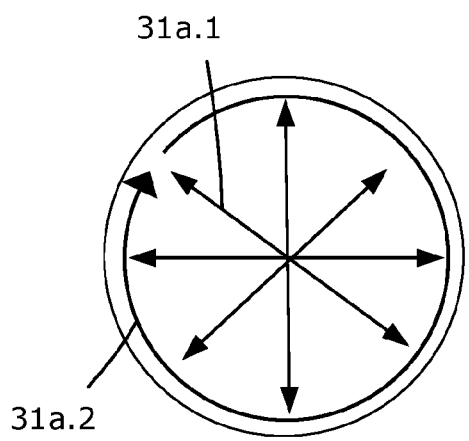
FIG. 4A to 4D illustrates different flow patterns depending on the eccentricity of an eccentric drive inducing the vibrations in a vibrational sieve with a normal sieve screen.
Figure 4B:
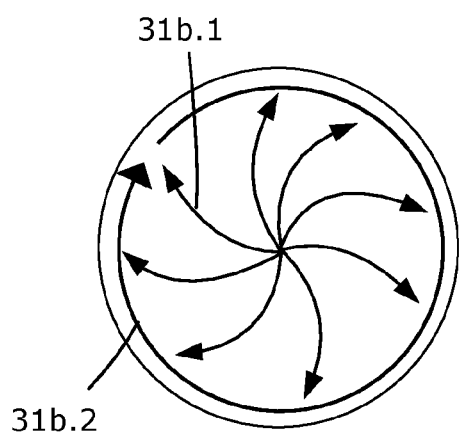
Figure 4C:
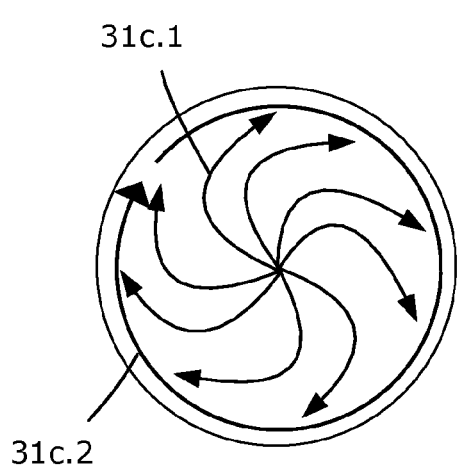
Figure 4D:
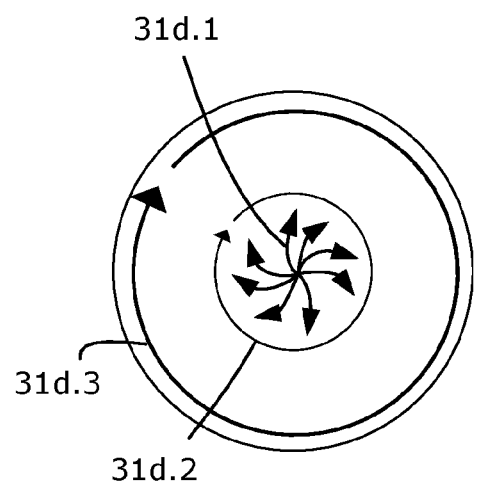

FIG. 4A to 4D illustrates different flow patterns depending on the eccentricity of an eccentric drive inducing the vibrations in a vibrational sieve with a normal sieve screen. The eccentricity is increased from the flow pattern shown in 4A to the flow pattern shown in 4D. The preferred flow pattern for the fractionation process according to the present disclosure is the flow pattern shown in FIGS. 4B and 4C and most preferably the flow pattern in FIG. 4B. The flow pattern in FIG. 4A shows lateral and almost straight radial lateral streamlines $31a.1$, and an orbital flow with orbital streamlines $31a.2$. The flow pattern in FIG. 4B shows curved lateral streamlines $31b.1$, and an orbital flow with orbital streamlines $31b.2$. The flow pattern in FIG. 4C shows curved lateral streamlines $31c.1$, and an orbital flow with orbital streamlines $31c.2$. The curvature of the lateral streamlines $31c.1$ for the flow pattern in 4C is larger than the curvature of the lateral streamlines $31b.1$ for the flow pattern in 4B. The flow pattern in FIG. 4D shows curved lateral streamlines $31d.1$, and a first orbital flow with orbital streamlines $31d.2$, and a second orbital flow with orbital streamlines $31d.3$.

Fractionation with a sieve guide 310 according to the present disclosure can be done by applying an eccentricity corresponding to a flow pattern as shown in FIG. 4B, and load granules onto the central portion of the sieve deck 130 defined by the circular portion 310.1 of the sieve guide 310. If the orbital flow is induced in the clockwise direction, as illustrated, an orbital flow will be induced along a guide wall of the circular portion. In the described example the orbital flow is clockwise. The circular portion comprises a radial opening arranged to guide the granules towards the outlet of the sieve deck. At the opening the granules will flow in the lateral direction, and the streamlines will be curved due to the eccentricity of the drive. The sieve guide 310 further comprise at least one radially extending lateral guide member adapted to follow the streamlines and thereby further supports the lateral flow an prevent granules to start orbiting on the sieve screen. A first lateral guide member 310.2 extends all the way from the circular portion to an outlet defined in the rim 135. A second lateral guide member 310.3 arranged counterclockwise to the first lateral guide member 310.2, extends from the circular portion towards the rim 135. However, a small gap 310.4 is defined by an end of the second lateral guide member and the rim 135 to allow granules, which has escaped the sieve guide 310 to enter or re-enter the guide and access the outlet in the rim 135.

In an exemplary embodiment is provided a sieve guide assembly comprising a circular sieve screen 190 and a sieve guide 310 mountable in a fractionating device for fractionating granules for tableting. The fractionating device comprises a drive adapted for: (i) in combination with a sieve screen without a sieve guide, inducing a lateral flow of granules defining lateral streamlines $31a.1$, $31b.1$, $31c.1$, $31d.1$ and an orbital flow defining orbital streamlines $31a.2$, $31b.2$, $31c.2$, $31d.2$, $31d.3$ on the sieve screen 190, and (ii) in combination with the sieve guide assembly, inducing a guided lateral flow of granules defining guided lateral streamlines 331.3 and a central guided orbital flow defining central orbital streamlines 331.2 on the sieve screen 190.

The sieve guide 310 is fixedly attached to the sieve screen 190, wherein the sieve guide 310 comprises a circular guide portion 310.1 adapted to guide the central guided orbital flow. The circular portion 310.1 is positioned centrally on the sieve screen 190 and thereby define a central loading area of the sieve screen for granules to be fractionated. The circular guide portion 310.1 comprises a first radial opening 310.5.

The sieve guide 310 further comprises a lateral guide portion adapted to guide the lateral flow of granules from the central loading area. The lateral guide portion comprises a first 310.2 and a second lateral guide member 310.3 extending from each side of the first radial opening 310.5 and to a periphery 190.1 of the sieve screen. The lateral guide members define a second radial opening 310.6 at the periphery, whereby the lateral guide members define a lateral flow path with an inlet at the first radial opening 310.5 and an outlet at the second radial opening 310.6. Thereby the sieve guide ensures a uniform travel distance from the loading area to the outlet at the second radial opening 310.6. Furthermore, the guide assembly is adapted to provide a uniform and effective exposure of the granules to the sieve screen.

The sieve guide is adapted to be mounted at a specific angular position by aligning the first lateral guide member with the outlet 132.

The specific angular position can be achieved, by adapting the sieve guide to be angularly adjustable during insertion and mounting, and wherein the sieve guide further is adapted to be fixed or clamped at the specific angular position.

Alternatively, the specific angular position can be achieved, by providing the sieve guide assembly with a key or a key-hole adapted to ensure the assembly is mounted in the specific angular position.

Additionally, in a further development of the embodiment of the sieve guide assembly, the first and the second lateral guide members are curved, and the shape of the curved guide members 310.2, 310.3 are adapted to the guided lateral streamlines 331.3 to provide a uniform thickness of a layer of the guided lateral flow of granules.

Additionally, in a further development of any of the previously described sieve guide assemblies, the sieve guide 310 circumference's an area of the sieve screen 190 defining a primary sieving 301 area comprising the central loading area and the lateral flow path, wherein the remaining area of the sieve screen 190 defines a secondary sieving area 302, and whereby less than 20% of the granules will be exposed to the sieve screen at the secondary sieving area.

Additionally, in a further development of any of the previously described sieve guide assemblies, the central orbital flow defines a direction of motion, wherein the first lateral guide member 310.2 is positioned in the direction of motion relative to the second lateral guide member 310.3, wherein the second lateral guide member 310.3 comprises an opening at the periphery 190.1 of the sieve screen adapted to allow granules escaping the sieve guide and following a peripheral orbital flow defining a peripheral orbital streamline 331.4 to enter the lateral flow path through the opening 310.4 in the second guide member.

Additionally, in a further development of any of the previously described sieve guide assemblies, the central orbital flow defines a direction of motion, wherein the first radial opening 310.5 is positioned at a first angular position and the second radial opening 310.6 is positioned at a second angular position, wherein the second angular position is in the direction of motion relative to the first angular position, whereby the lateral flow path from the central loading area is curved.

Additionally, in a further development of any of the previously described sieve guide assemblies, an arch length defined by the second radial opening 310.6 and a center 303 of the sieve screen 190 defines a circular sector 304 with an angle smaller than 70 degrees, wherein granules can flow from first radial opening 310.5 to the second radial opening 310.6 to define one or more guided lateral streamlines of the guided lateral streamlines 331.2, completely within the area defined by the circular sector 304.

Alternatively, in a further development of any of the previously described sieve guide assemblies, an arch length defined by the second radial opening 310.6 and a center 303 of the sieve screen 190 defines a circular sector 304 with an angle between 40 and 60 degrees, wherein granules can flow from first radial opening 310.5 to the second radial opening 310.6 to define one or more guided lateral streamlines of the guided lateral streamlines 331.2, completely within the area defined by the circular sector 304.

Additionally, in a further development of any of the previously described sieve guide assemblies, the central loading area and the lateral flow path define a primary sieving area, which is a fraction of the total area of the sieve screen, and wherein the fraction is in the range of 10-30%.

In an exemplary embodiment is provided a fractionating device for fractionating granules for tableting, wherein the fractionating device comprises a sieve guide assembly according to any of previously described embodiments, and a drive adapted for, in combination with the sieve guide assembly, inducing a guided lateral flow of granules defining guided lateral streamlines 331.3 and a central guided orbital flow defining central orbital streamlines 331.2 on the sieve screen 190.

Additionally, in a further development of the fractionating device, the fractionating device comprises a sieve deck 130, wherein the sieve deck comprises a tubular deck portion comprising a rim 135, wherein the tubular portion comprises a first end defining an inlet 131 and a second end adapted for assembly with the sieve screen (190), wherein the rim 135 comprises an opening defining an outlet 132. The inlet 131 is adapted to enable loading of granules onto the central loading area of the sieve screen 190, and the outlet 132 is aligned with the second radial opening 310.6 and thereby adapted to enable fractionated granules to exit from the sieve screen.

Additionally, in a further development of any of the previously described fractionating devices, the rim 135 supports a peripheral orbital flow for granules escaping the sieve guide defining a peripheral orbital streamline 331.4 and a direction of motion, wherein the first lateral guide member 310.2 is positioned in the direction of motion relative to the second lateral guide member 310.3. The second lateral guide member 310.3 comprises an opening at the periphery 190.1 of the sieve screen adapted to allow granules escaping the sieve guide and following the peripheral orbital flow to enter the lateral flow path through the opening 310.4 in the second guide member.

Additionally, in a further development of any of the previously described fractionating devices, the fractionating device comprises a sieve guide assembly according to any the previously described embodiments, and a drive adapted for: (i) in combination with a sieve screen without a sieve guide, inducing a lateral flow of granules defining lateral streamlines 31a.1. 31b.1, 31c.1, 31d.1 and an orbital flow defining orbital streamlines 31a.2. 31b.2, 31c.2, 31d.2, 31d.3 on the sieve screen 190, and (ii) in combination with the sieve guide assembly, inducing a guided lateral flow of granules defining guided lateral streamlines 331.3 and a central guided orbital flow defining central orbital streamlines 331.2 on the sieve screen 190.

Additionally, in a further development of any of the previously described fractionating devices, the fractionating device further comprises a vibrator arranged to vibrate and deblind the sieve screen 190. The vibrator may be an ultrasonic vibrator.

In an exemplary embodiment is provided a method of fractionating granules comprising SNAC using the fractionating device according to any previously described fractionating devices wherein the method comprises fractionating the granules and uniformly exposing the granules to the sieve screen.

Additionally, in a further development of the described method, the method further comprising guiding the granules along the lateral flow path in a layer of uniform thickness.

Additionally, in a further development of any of the previously described methods, the method, further comprising continuously fractionating granules.

Additionally, in a further development of any of the previously described methods, the method further comprises providing a roller compactor in-line with the fractionating device, whereby the roller compactor is feeding unfractionated granules into the fractionating device.

Additionally, in a further development of the previously described method, the roller compactor feeds directly into the fractionating device, whereby there is no accumulation and a steady state feed rate to the fractionating device, i.e., there is no accumulating tank or buffer between the roller compactor and the fractionating device.

Additionally, in a further development of any of the previously described methods, the method further comprises exposing a major portion of the granules to the sieve screen at a primary sieving area comprising the central loading area and the lateral flow path, wherein the major portion of the granules comprises more than 80% of the total amount of unfractionated granules.

Additionally, in a further development of any of the previously described methods, the method further comprises exposing a minor portion of the granules to the sieve screen at a secondary sieving area comprising the area of the sieve screen not being the central loading area and not being the area of lateral flow path, wherein the minor portion comprises less than 20% of the total amount of unfractionated granules.

In an exemplary embodiment is provided a sieve deck assembly comprising a sieve deck 130 comprising a tubular deck portion comprising a rim 135, wherein the tubular portion comprises a first end defining an inlet 131 and a second end adapted for assembly with the sieve screen 190 and the sieve screen frame 134, wherein the rim 135 comprises an opening defining an outlet 132. The sieve deck assembly further comprises a sieve guide assembly according to any of the previously described embodiments.

In an exemplary embodiment is provided a sieve guide 310 for a sieve deck assembly mountable in a fractionating device for fractionating granules for tableting. The fractionating device comprises a sieve screen 190, and a drive adapted for: (i) in combination with the sieve screen without a sieve guide, inducing a lateral flow of granules defining lateral streamlines 31a.1. 31b.1, 31c.1, 31d.1 and an orbital flow defining orbital streamlines 31a.2. 31b.2, 31c.2, 31d.2, 31d.3 on the sieve screen 190, and (ii) in combination with the sieve guide 310 and the sieve screen 190, inducing a guided lateral flow of granules defining guided lateral streamlines 331.3 and a central guided orbital flow defining central orbital streamlines 331.2 on the sieve screen 190.

The sieve deck assembly further comprises a sieve screen frame 130 supporting the sieve screen 190. The sieve deck 130 comprises a tubular deck portion comprising a rim 135. The tubular portion comprises a first end defining an inlet 131 and a second end adapted for assembly with the sieve screen 190 and the sieve screen frame 134. The rim 135 comprises an opening defining an outlet 132.

For the sieve deck assembly in an assembled state, the sieve deck 130 is assembled with the sieve screen frame 134 and the sieve screen 190, whereby the inlet 131 is adapted to enable loading of granules onto a central loading area of the sieve screen 190. Furthermore, the outlet 132 is adapted to enable a fraction of the loaded granules to flow out of the sieve deck assembly.

The sieve guide 310 comprises a circular portion 310.1, wherein the sieve guide is adapted to be fixedly attached to the sieve screen 190 and whereby the circular portion defines the central loading area.

The circular portion 310.1 is adapted to guide the central guided orbital flow, and the circular portion further comprises an opening 310.5 for guiding granules from the central orbital flow to the lateral guided flow.

The sieve guide 310 further comprises a lateral portion extending from the opening 310.5 of the circular portion to the outlet 132, wherein the lateral portion is adapted for guiding the granules along the guided lateral flow.

The lateral portion is adapted to follow the streamlines of the guided lateral flow, whereby it is ensured that the granules can flow in a layer with a uniform thickness from the central portion and to the outlet.

First List of Embodiments

1. A sieve guide assembly comprising a circular sieve screen 190 and a sieve guide 310 mountable in a fractionating device for fractionating granules for tableting, wherein the fractionating device comprises a drive adapted for: (i) in combination with a sieve screen without a sieve guide, inducing a lateral flow of granules defining lateral streamlines 31a.1. 31b.1, 31c.1, 31d.1 and an orbital flow defining orbital streamlines 31a.2. 31b.2, 31c.2, 31d.2, 31d.3 on the sieve screen 190, and (ii) in combination with the sieve guide assembly, inducing a guided lateral flow of granules defining guided lateral streamlines 331.3 and a central guided orbital flow defining central orbital streamlines 331.2 on the sieve screen 190;
wherein the sieve guide 310 is fixedly attached to the sieve screen 190, wherein the sieve guide 310 comprises:
 a circular guide portion 310.1 adapted to guide the central guided orbital flow, wherein the circular portion 310.1 is positioned centrally on the sieve screen 190 and thereby defining a central loading area of the sieve screen for granules to be fractionated, and wherein the circular guide portion 310.1 comprises a first radial opening 310.5,
 a lateral guide portion adapted to guide the lateral flow of granules from the central loading area, comprising a first 310.2 and a second lateral guide member 310.3 extending from each side of the first radial opening 310.5 and to a periphery 190.1 of the sieve screen, wherein the lateral guide members define a second radial opening 310.6 at the periphery, whereby the lateral guide members define a lateral flow path with an inlet at the first radial opening 310.5 and an outlet at the second radial opening 310.6, and thereby ensuring a uniform travel distance from the loading area to the outlet at the second radial opening 310.6; and
whereby the guide assembly is adapted to provide a uniform and effective exposure of the granules to the sieve screen.

2. A sieve guide assembly according to embodiment 1, wherein the first and the second lateral guide members are curved, and wherein the shape of the curved guide members 310.2, 310.3 are adapted to the guided lateral streamlines 331.3 to provide a uniform thickness of a layer of the guided lateral flow of granules.

3. A sieve guide assembly according to any of embodiments 1 and 2, wherein the sieve guide 310 circumference's an area of the sieve screen 190 defining a primary sieving 301 area comprising the central loading area and the lateral flow path, wherein the remaining area of the sieve screen 190 defines a secondary sieving area 302, and whereby less than 20% of the total amount of granules will be exposed to the sieve screen at the secondary sieving area.

4. A sieve guide assembly according to any of the previous embodiments, wherein the central orbital flow defines a direction of motion, wherein the first lateral guide member 310.2 is positioned in the direction of motion relative to the second lateral guide member 310.3, wherein the second lateral guide member 310.3 comprises an opening at the periphery 190.1 of the sieve screen adapted to allow granules escaping the sieve guide and following a peripheral orbital flow defining a peripheral orbital streamline 331.4 to enter the lateral flow path through the opening 310.4 in the second guide member.

5. A sieve guide assembly according to embodiment 1, wherein the central orbital flow defines a direction of motion, wherein the first radial opening 310.5 is positioned at a first angular position and the second radial opening 310.6 is positioned at a second angular position, wherein the second angular position is in the direction of motion relative to the first angular position, whereby the lateral flow path from the central loading area is curved.

6. A sieve guide assembly according to any of the previous embodiments, wherein an arch length defined by the second radial opening 310.6 and a center 303 of the sieve screen 190 defines a circular sector 304 with an angle smaller than 70 degrees, wherein granules can flow from first radial opening 310.5 to the second radial opening 310.6 to define one or more guided lateral streamlines of the guided lateral streamlines 331.2, completely within the area defined by the circular sector 304.

7. A sieve guide assembly according to any of the embodiments 1-6, wherein an arch length defined by the second radial opening 310.6 and a center 303 of the sieve screen 190 defines a circular sector 304 with an angle between 40 and 60 degrees, wherein granules can flow from first radial opening 310.5 to the second radial opening 310.6 to define one or more guided lateral streamlines of the guided lateral streamlines (331.2), completely within the area defined by the circular sector 304.

8. A sieve guide assembly according to any of the previous embodiments, wherein the central loading area and the lateral flow path define a primary sieving area, which is the fraction of the total area of the sieve screen, and wherein the fraction is in the range of 10-30%.

9. A fractionating device for fractionating granules for solid dosage forms, such as tablets, capsules or sachets, wherein the fractionating device comprises a sieve guide assembly according to any of embodiments 1-8, and a drive adapted for, in combination with the sieve guide assembly, inducing a guided lateral flow of granules defining guided lateral streamlines 331.3 and a central guided orbital flow defining central orbital streamlines 331.2 on the sieve screen 190.

10. A fractionating device according to embodiment 9, wherein the fractionating device further comprises sieve deck 130, wherein the sieve deck comprises a tubular deck portion comprising a rim 135, wherein the tubular portion comprises a first end defining an inlet 131 and a second end adapted for assembly with the sieve screen 190, wherein the rim (135) comprises an opening defining an outlet 132; wherein the inlet 131 enables loading of granules onto the central loading area of the sieve screen 190, and the outlet 132 is aligned with the second radial opening 310.6 and thereby enables fractionated granules to exit.

11. A fractionating device according to embodiment 10, wherein the rim 135 supports a peripheral orbital flow for granules escaping the sieve guide defining a peripheral orbital streamline 331.4 and a direction of motion, wherein the first lateral guide member 310.2 is positioned in the direction of motion relative to the second lateral guide member 310.3, wherein the second lateral guide member 310.3 comprises an opening at the periphery 190.1 of the sieve screen adapted to allow granules escaping the sieve guide and following the peripheral orbital flow to enter the lateral flow path through the opening 310.4 in the second guide member.

12. A fractionating device for fractionating granules for tableting, wherein the fractionating device comprises a sieve guide assembly according to any of embodiments 1-8, and a drive adapted for: (i) in combination with a sieve screen without a sieve guide, inducing a lateral flow of granules defining lateral streamlines 31a.1. 31b.1, 31c.1, 31d.1 and an orbital flow defining orbital streamlines 31a.2. 31b.2, 31c.2, 31d.2, 31d.3 on the sieve screen 190, and (ii) in combination with the sieve guide assembly, inducing a guided lateral flow of granules defining guided lateral streamlines 331.3 and a central guided orbital flow defining central orbital streamlines 331.2 on the sieve screen 190.

13. A fractionating device according to any of the embodiments 9-12 further comprising a vibrator arranged to vibrate and deblind the sieve screen 190.

14. A method of fractionating granules comprising SNAC using the fractionating device according to any of embodiments 9-13 comprising fractionating the granules and uniformly exposing the granules to the sieve screen.

15. A method of fractionation according to embodiment 14 further comprising guiding the granules along the lateral flow path in a layer of uniform thickness.

16. A method of fractionation according to any of embodiments 14-15 further comprising continuously fractionating granules.

17. A method according to any of embodiments 14-16 further comprising a roller compactor in-line with the fractionating device, whereby the roller compactor is feeding unfractionated granules into the fractionating device.

18. A method according to embodiment 17, wherein the roller compactor feeds directly into the fractionating device, whereby there is no accumulation and a steady state feed rate to the fractionating device.

19. A method of fractionation according to any of embodiments 14-18 further comprising exposing a major portion of the granules to the sieve screen at a primary sieving area comprising the central loading area and the lateral flow path, wherein the major portion of the granules comprises more than 80% of the total amount of unfractionated granules.

20. A method of fractionation according to any of embodiments 14-19 further comprising exposing a minor portion of the granules to the sieve screen at a secondary sieving area comprising the area of the sieve screen not being the central loading area and not being the area of lateral flow path, wherein the minor portion comprises less than 20% of the total amount of unfractionated granules.

21. A sieve deck assembly comprising a sieve deck 130 comprising a tubular deck portion comprising a rim 135, wherein the tubular portion comprises a first end defining an inlet 131 and a second end adapted for assembly with the sieve screen 190 and the sieve screen frame 134, wherein the rim 135 comprises an opening defining an outlet 132; a sieve guide assembly according to any of embodiments 1-8.

22. A sieve guide 310 for a sieve deck assembly mountable in a fractionating device for fractionating granules for solid dosage forms such as tablets, capsule or sachets, wherein the fractionating device comprises a sieve screen 190, and a drive adapted for: (i) in combination with the sieve screen without a sieve guide, inducing a lateral flow of granules defining lateral streamlines 31a.1. 31b.1, 31c.1, 31d.1 and an orbital flow defining orbital streamlines 31a.2. 31b.2, 31c.2, 31d.2, 31d.3 on the sieve screen 190, and (ii) in combination with the sieve guide 310 and the sieve screen 190, inducing a guided lateral flow of granules defining guided lateral streamlines 331.3 and a central guided orbital flow defining central orbital streamlines 331.2 on the sieve screen 190;

wherein the sieve deck assembly further comprises a sieve deck 130 and a sieve screen frame 134 supporting the sieve screen 190;

wherein the sieve deck 130 comprises a tubular deck portion comprising a rim 135, wherein the tubular portion comprises a first end defining an inlet 131 and a second end adapted for assembly with the sieve screen 190 and the sieve screen frame 134, wherein the rim 135 comprises an opening defining an outlet 132; and wherein, for the sieve deck assembly in an assembled state, the sieve deck 130 is assembled with the sieve screen frame 134 and the sieve screen 190, whereby:

the inlet 131 enables loading of granules onto a central loading area of the sieve screen 190, the outlet 132 enables a fraction of the loaded granules to flow out of the sieve deck assembly;

wherein the sieve guide 310 comprises a circular portion 310.1, wherein the sieve guide is adapted to be fixedly attached to the sieve screen (190) and whereby the circular portion defines the central loading area;

wherein the circular portion 310.1 is adapted to guide the central guided orbital flow, wherein the circular portion further comprises an opening 310.5 for guiding granules from the central orbital flow to the lateral guided flow;

wherein the sieve guide 310 further comprises a lateral portion extending from the opening 310.5 of the circular portion to the outlet 132, wherein the lateral portion is adapted for guiding the granules along the guided lateral flow, wherein the lateral portion is adapted to follow the streamlines of the guided lateral flow, whereby it is ensured that the granules can flow in a layer with a uniform thickness from the central portion and to the outlet.

23. A composition comprising granules of a salt of NAC, wherein the composition has 8-20% w/w of granules smaller than (<) 90 μm such as 8-18, 9-15 or such as 9-12% w/w of granules smaller than (<) 90 μm.

24. A composition comprising granules of a salt of NAC, wherein the composition has a funnel flowability below 50 g/s, such as between 5-40 g/s, 8-30 g/s, 5-30 g/s, 10-20 g/s or such as between 12-18 g/s.

25. A composition comprising granules of a salt of NAC, wherein the composition has a compressibility above 15%.

26. A composition comprising granules of a salt of NAC, wherein the composition has a score below 0 for principal component 1, such as a PC1 score of −2 to 0, such as −2 to −0.5, such a −2 to −0.7.

27. The composition according to embodiments 23, 25 or 26, wherein the composition has a funnel flowability below 50 g/s, such as between 5-40 g/s, 8-30 g/s, 5-30 g/s, 10-20 g/s or such as between 12-18 g/s.

28. The composition according to embodiments 24, 25 or 26, wherein the composition has more than 8% w/w of granules smaller than (<) 90 μm such as 8-20, 9-15 or such as 9-12% w/w of granules smaller than (<) 90 μm.

29. A composition comprising granules of a salt of NAC, wherein the composition
  a) has 8-20% w/w of granules smaller than (<) 90 μm such as 8-18, 9-15 or such as 9-12% w/w,
  a) has compressibility above 15%,
  b) has a funnel flowability below 50 g/s, such as between 5-40 g/s, 8-30 g/s, 5-30 g/s, 10-20 g/s or such as between 12-18 g/s and/or has a score below 0 for principal component 1, such as a PC1 score of −2 to 0, such as −2 to −0.5, such a −2 to −0.7.

30. A composition comprising granules of a salt of NAC, wherein the composition
  a) has 8-20% w/w of granules smaller than (<) 90 μm such as 8-18, 9-15 or such as 9-12% w/w,
  b) has a compressibility above 15%,
  c) has a funnel flowability below 50 g/s, such as between 5-40 g/s, 8-30 g/s, 5-30 g/s, 10-20 g/s or such as between 12-18 g/s and
  d) has a score below 0 for principal component 1, such as a PC1 score of −2 to 0, such as −2 to −0.5, such a −2 to −0.7.

31. The composition according to any of the embodiments 23-30, wherein the flowability is measured with a funnel orifice of 25 mm, such as by the method described in example 4.

32. The composition according to any of the embodiments 23-31, wherein the 5% w/w of granules smaller than (<) 90 μm is measured by analytical sieving, such as described in method 3.

33. The composition according to any of the embodiments 23-32, wherein the PC1 score is determined as described in example 5.

34. The composition according to any of the embodiments 23-33, wherein the compressibility is determined as described in example 3.

35. The composition according to any of the embodiments 23-34, wherein the salt of NAC is SNAC.

36. The composition according to any of the embodiments 23-35, wherein the granules further comprise a lubricant.

37. The composition according to embodiment 36, wherein the lubricant is magnesium stearate.

38. The composition according to any of the embodiments 23-37, wherein the granules further comprise a filler.

39. The composition according to embodiment 38, wherein the filler is microcrystalline cellulose (MCC).

While certain features of the invention have been illustrated and described herein, many modifications, substitutions, changes, and equivalents will now occur to those of ordinary skill in the art. It is, therefore, to be understood that the appended examples are intended to cover all such modifications and changes as fall within the true spirit of the invention.

Second List of Embodiments

1. A sieve guide assembly comprising a circular sieve screen 190 and a sieve guide 310 mountable in a fractionating device for fractionating granules for tableting, wherein the fractionating device comprises a tubular rim portion with an outlet 132, and a drive adapted for in combination with the sieve guide assembly, inducing a guided lateral flow of granules defining guided lateral streamlines 331.3 with a direction of the flow, and a central guided orbital flow defining central orbital streamlines 331.2 with a direction of the flow on the sieve screen 190, wherein the outlet 132 is provided as an opening in the tubular rim portion extending in the upstream direction from a first to a second side, as defined by the direction of the central orbital flow;

wherein the sieve guide 310 is fixedly attached to the sieve screen 190, wherein the sieve guide 310 comprises:
  a circular guide portion 310.1 adapted to guide the central guided orbital flow, wherein the circular portion 310.1 is positioned centrally on the sieve screen 190 and thereby defining a central loading area of the sieve screen for granules to be fractionated, and wherein the circular guide portion 310.1 comprises a first radial opening 310.5 extending in an upstream direction from a first to a second side, as defined by the central guided orbital flow,
  a lateral guide portion adapted to guide the lateral flow of granules from the central loading area, comprising a first guide member 310.2 extending from the first side of the first radial opening 310.5 and to a periphery 190.1 of the sieve screen,
wherein the sieve guide assembly is adapted to be mounted in the fractionating device with the first lateral guide member 310.2 aligned with the first side of the outlet 132, whereby the first lateral guide member define a guided lateral flow path from an inlet at the first radial opening 310.5 and towards the periphery 190.1 along an upstream side of the first lateral guide member 310.2, as defined by the central guided orbital flow, when the sieve guide assembly is mounted in the fractionating device.

2. A sieve guide assembly according to embodiment 1, wherein the first lateral guide member is curved.

3. A sieve guide assembly according to any of embodiments 1 or 2, further comprising a sieve frame 134 supporting the sieve screen 190 and the sieve guide 310, wherein the frame comprises a key 134.1 for engagement with the fractionating device and for mounting the sieve guide assembly at a specific angular position ensuring alignment with the outlet 132.

4. A sieve guide assembly according to any of the previous embodiments, wherein the lateral guide portion further comprise a second lateral guide member 310.3 extending from the second side of the first radial opening 310.5 towards the periphery, wherein the first and the second lateral guide members define a second radial opening 310.6 at the periphery 190.1 of the screen.

5. A sieve guide assembly according to embodiment 4, wherein the first and the second lateral guide members are curved, and wherein the shape of the curved guide members 310.2, 310.3 are adapted to the guided lateral streamlines 331.3 to provide a uniform thickness of a layer of the guided lateral flow of granules.

6. A sieve guide assembly according to any of the embodiments 2-5, wherein the curvature of a curved lateral guide member is defined by a circle with a center on the downstream side of the curved lateral guide member, as defined by the direction of the central guided orbital flow.

7. A sieve guide assembly according to any of the previous embodiments, wherein the sieve guide 310 marks an area of the sieve screen 190 defining a primary sieving 301 area comprising the central loading area and the lateral flow path, wherein the remaining area of the sieve screen 190 defines a secondary sieving area 302, and whereby less than 20% of the total amount of granules will be exposed to the sieve screen at the secondary sieving area.

8. A sieve guide assembly according to embodiment 7, wherein the sieve guide marks the primary sieving area by partially enclosing the area.

9. A sieve guide assembly according to any of the embodiments 4-8, wherein the second lateral guide member 310.3 comprises an opening at the periphery 190.1 of the sieve screen adapted to allow granules escaping the sieve guide and following a peripheral orbital flow defining a peripheral orbital streamline 331.4 to enter the lateral flow path through the opening 310.4 in the second guide member.

10. A sieve guide assembly according to any of the embodiments 4-9, wherein the first radial opening 310.5 is positioned at a first angular position and the second radial opening 310.6 is positioned at a second angular position, wherein the second angular position is in the direction of motion relative to the first angular position, whereby the lateral flow path from the central loading area is curved.

11. A sieve guide assembly according to any of the previous embodiments, wherein an arch length defined by the second radial opening 310.6 and a center 303 of the sieve screen 190 defines a circular sector 304 with an angle smaller than 70 degrees, wherein granules can flow from first radial opening 310.5 to the second radial opening 310.6 to define one or more guided lateral streamlines of the guided lateral streamlines 331.2, completely within the area defined by the circular sector 304.

12. A sieve guide assembly according to any of the embodiments 1-11, wherein an arch length defined by the second radial opening 310.6 and a center 303 of the sieve screen 190 defines a circular sector 304 with an angle between 40 and 60 degrees, wherein granules can flow from first radial opening 310.5 to the second radial opening 310.6 to define one or more guided lateral streamlines of the guided lateral streamlines 331.2, completely within the area defined by the circular sector 304.

13. A sieve guide assembly according to any of the previous embodiments, wherein the central loading area and the lateral flow path define a primary sieving area, which is a fraction of the total area of the sieve screen, and wherein the fraction is in the range of 10-30%.

14. A fractionating device for fractionating granules for solid dosage forms, such as tablets, capsules, or sachets, wherein the fractionating device comprises a sieve guide assembly according to any of embodiments 1-13, a rim portion with an outlet 132 and a drive adapted for, in combination with the sieve guide assembly, inducing a guided lateral flow of granules defining guided lateral streamlines 331.3 with a direction of the flow and a central guided orbital flow defining central orbital streamlines 331.2 with a direction of the flow on the sieve screen 190.

METHODS AND EXAMPLES

Methods and Examples

Method 1: Granulation

Salcaprozate sodium (SNAC) and magnesium stearate were blended in a diffusion mixer at 25 rpm for 50 min and then microcrystalline cellulose was added and all components blended for another 20 min prior to granulation. Granulation was carried out by roller compaction on a Gerteis roller compactor using knurled rolls, a 0.63 mm wire mesh screen, and a granulator speed of no less than 75 rpm. The speed was set at 5.3 rpm and a compaction force of 7 kN/cm were applied at a gap of 2 mm. Subsequent to dry granulation, comminution was performed of the moldings into granules before the granules entered the vibrational sieve as described in method 2.

Method 2: Fractionation Using Vibrational Sieving

Fractionation of granules containing salcaprozate sodium (SNAC), microcrystalline cellulose (MCC), and magnesium stearate was performed by vibrational sieving on a Russell Finex 22" placed in-line with the roller compactor. The vibrational sieve was set at a horizontal movement of 20°, a vertical movement of E, and a constant ultrasonication level for the lower sieve deck. The lower deck was installed with a 90 μm sieve mesh with or without the sieve guide. The "granule fraction" obtained from above the lower deck is the desired granules composition and called granule product. The "granule fraction" obtained from below the lower deck is not desirable and called the undersized granules.

Method 3: Sieve Analysis

The particle size, i.e. the amount distribution, was determined by analytical sieving (Retsch AS200) using a sample size of around 50 g, a sieving time of 6 min, an amplitude of 1.5 mm, a continuous sieving mode, and an analytical sieve tower consisting of a bottom and sieve mesh sizes of 63 (optional), 90, 125, 180, 250, 355, 500, and 710 μm. The amounts on each sieve and bottom were determined and the relative amount distribution for the particle size was calculated.

Example 1: Yield of Granule Product

The yield of granule product (>90 μm) was measured after fractionation according to method 2. The yields were calculated as percentages of the amount being roller compacted and the results are presented in Table 1.

TABLE 1

| Yields following fractionation. | | |
|---|---|---|
| Sieve setup | Under-sized granules (<90 μm) | Granule product (>90 μm) |
| Sieve with guide | 9% w/w | 84% w/w |
| Sieve without guide | 26% w/w | 65% w/w |

The results show that the yields of under-sized granules (<90 μm) and of granule product (>90 μm) were impacted by the sieve guide. The results demonstrate that the yield of granule product (>90 μm) increases when the fractionation is performed with the sieve guide.

Example 2: Particle Size Distribution by Sieve Analysis

Granules were fractionated according to method 2 and the resulting granule products (>90 μm) were subjected to particle size analyses by sieve analysis (Method 3). The analysis was performed on granule products from two tests (test 1 and test 2) with two (table 2.1) and three (table 2.2) replicates, respectively. Results are included in table 2.1 and table 2.2 below.

TABLE 2.1

Particle size distribution of granule product (test 1)

| Sieve setup | Replicate | Amount <90 μm | Amount between 90 to 355 μm | Amount >355 μm |
|---|---|---|---|---|
| Sieve with guide | 1 | 9.0% | 59.7% | 31.4% |
| Sieve with guide | 2 | 10.7% | 60.9% | 28.5% |
| Sieve with guide | Average | 9.8% | 60.3% | 29.9% |
| Sieve without guide | 1 | 7.7% | 65.5% | 26.8% |
| Sieve without guide | 2 | 5.4% | 57.3% | 37.4% |
| Sieve without guide | Average | 6.5% | 61.4% | 32.1 |

TABLE 2.2

Particle size distribution of granule product (test 2)

| Sieve setup | Replicate | Amount <90 μm | Amount between 90 to 355 μm | Amount >355 μm |
|---|---|---|---|---|
| Sieve with guide | 1 | 10.8% | 65.5% | 23.8% |
| Sieve with guide | 2 | 9.8% | 66.1% | 24.0% |
| Sieve with guide | 3 | 10.9% | 65.4% | 23.8% |
| Sieve with guide | Average | 10.5% | 65.7% | 23.9% |
| Sieve without guide | 1 | 6.3% | 64.6% | 29.1% |
| Sieve without guide | 2 | 6.2% | 63.9% | 29.9% |
| Sieve without guide | 3 | 6.3% | 63.2% | 30.5% |
| Sieve without guide | Average | 6.3% | 63.9% | 29.9% |

The results show that the granule product contains larger amounts of particles <90 μm when obtained using the sieve guide compared to the granule product obtained using the sieve without guide. Likewise, the results show that the granule product contains smaller amounts of particles >355 μm when obtained using the sieve guide compared to the product obtained using a sieve without guide. Analysis of granule product (>90 μm) from further two tests (test 3 and test 4) gave similar results.

Example 3: Densities and Compressibility

Granules were fractionated according to method 2 and the resulting granule products (>90 μm) from test 2 were subjected to density analyses using 6 replicates. The bulk density was determined in a 100 mL graduated cylinder using a sample size of around 50 g. The volume of the sample was determined, and the bulk density calculated. The tap density was determined using the settling volume of the same sample after 5000 taps and the compressibility was calculated as the difference between the tap density and the bulk density divided by the tap density and given as a percentage. Results, including average values, are shown in table 3 below.

TABLE 3

Bulk densities, Tap density and Compressibility after sieving (test 2)

| Sieve setup | Replicate | Bulk density | Tap density | Compressibility |
|---|---|---|---|---|
| Sieve with guide | 1 | 0.528 g/mL | 0.633 g/mL | 16.7% |
| Sieve with guide | 2 | 0.529 g/mL | 0.633 g/mL | 16.3% |
| Sieve with guide | 3 | 0.529 g/mL | 0.629 g/mL | 16.0% |
| Sieve with guide | 4 | 0.530 g/mL | 0.630 g/mL | 16.0% |
| Sieve with guide | 5 | 0.534 g/mL | 0.642 g/mL | 16.8% |
| Sieve with guide | 6 | 0.536 g/mL | 0.640 g/mL | 16.3% |
| Sieve with guide | Average | 0.53 g/mL | 0.64 g/mL | 16% |
| Sieve without guide | 1 | 0.507 g/mL | 0.587 g/mL | 13.7% |
| Sieve without guide | 2 | 0.504 g/mL | 0.581 g/mL | 13.3% |
| Sieve without guide | 3 | 0.519 g/mL | 0.586 g/mL | 11.5% |
| Sieve without guide | 4 | 0.507 g/mL | 0.586 g/mL | 13.4% |
| Sieve without guide | 5 | 0.518 g/mL | 0.592 g/mL | 12.5% |
| Sieve without guide | 6 | 0.517 g/mL | 0.587 g/mL | 12.0% |
| Sieve without guide | Average | 0.51 g/mL | 0.59 g/mL | 13% |

The results show that the granule product obtained by fractionation using a sieve with guide has higher bulk and tap densities than the granule product obtained using a sieve without guide. Furthermore, the results show that the granule product obtained by fractionation using a sieve with guide has a higher compressibility (>15%) than the granule product obtained using a sieve without guide (<15%). Analysis of granule product (>90 µm) from further two tests (test 3 and test 4) gave similar results.

Example 4: Funnel Flowability—Using a Funnel with Orifice of 25 mm

Granules were fractionated according to method 2 and the resulting granule products (>90 µm) from test 2, test 3, and test 4 were subjected to flowability analyses. The funnel flowability was determined using a funnel with a bottom orifice of 25 mm in diameter and using a sample size of 100-250 g. The time while emptying sample through the funnel orifice and the amount emptied in that time span were determined and the funnel flowability calculated. Results are included in table 4.

TABLE 4

Flowabilities after sieving

| Sieve setup | Replicate | Flowability (test 2) | Flowability (test 3) | Flowability (test 4) |
|---|---|---|---|---|
| Sieve with guide | 1 | 13.2 g/s | 14.0 g/s | 12.8 g/s |
| Sieve with guide | 2 | 16.4 g/s | 18.6 g/s | 17.3 g/s |
| Sieve with guide | 3 | 15.2 g/s | 22.3 g/s | 17.6 g/s |
| Sieve with guide | Average | 15 g/s | 18 g/s | 16 g/s |
| Sieve without guide | 1 | 53.3 g/s | 46.5 g/s | 38.5 g/s |
| Sieve without guide | 2 | 70.9 g/s | 52.3 g/s | 50.7 g/s |
| Sieve without guide | 3 | 53.2 g/s | 55.0 g/s | 50.7 g/s |
| Sieve without guide | Average | 59 g/s | 51 g/s | 47 g/s |

The results show that the granule product obtained by fractionation performed using a sieve with guide has a lower funnel flowability (<25 g/s) than a granule product obtained using a sieve without guide (>40 g/s).

Example 5: Near Infra-Red Spectroscopy

Granules were fractionated according to method 2 and the resulting granule products (>90 µm) from test 2, test 3, and test 4 were subjected to near infra-red (NIR) spectroscopy using a Bruker MPA. The NIR spectra were subjected to a principal component analysis and a model was established with mean centering as pre-processing of the spectra and with the score from Principle Component 1 explaining more than (>) 90% of the variance. The scores are presented in table 5.

TABLE 5

Scores of principal component 1 (PC1) for NIR spectra after sieving

| Sieve setup | Replicate | PC1 score (test 2) | PC1 score (test 3) | PC1 score (test 4) |
|---|---|---|---|---|
| Sieve with guide | 1 | −1.1 | −0.8 | −1.1 |
| Sieve with guide | 2 | −1.0 | −0.8 | −1.3 |
| Sieve with guide | 3 | −1.4 | −1.0 | −1.7 |
| Sieve with guide | Average | −1.1 | −0.9 | −1.4 |
| Sieve without guide | 1 | 0.8 | 2.1 | 1.3 |
| Sieve without guide | 2 | 0.9 | 1.1 | 1.6 |

TABLE 5-continued

Scores of principal component 1 (PC1) for NIR spectra after sieving

| Sieve setup | Replicate | PC1 score (test 2) | PC1 score (test 3) | PC1 score (test 4) |
|---|---|---|---|---|
| Sieve without guide | 3 | 1.0 | 1.2 | 1.0 |
| Sieve without guide | Average | 0.9 | 1.5 | 1.3 |

The results show that the NIR spectra for the granule product obtained using the sieve with guide are significantly different from the NIR spectra for the granule product obtained without use of the sieve guide. The difference determined by NIR spectra is caused by physical properties of the granules resulting in a scattering effect of the NIR spectra. The difference is very clear as the PC1 scores are either around −1 or around 1, and thus demonstrating a clear separation.

Example 6: Tablet Mechanical Strength

To evaluate the impact on tablet mechanical strength of granules obtained with the use of the sieve guide and without the use of the sieve guide, a series of tablets were produced using the granule products from test 2, test 3, and test 4 described above. The tablets were prepared as composition type E in Exp. X, described in WO 2013/139695 using the "Granule products" obtained from test 2, test 3, and test 4 as the first granules and with the exception that only 23 mg MCC were included in the second granules. The tablets were compressed at a main compression force of around 3 to 15 kN and at a rotation speed of 20 rpm using a Fette 102i tablet press. The composition is specified here below.

| | Ingredient | mg/tablet |
|---|---|---|
| First granule "Granule product" | SNAC | 300 |
| | MCC | 57 |
| | Magnesium stearate | 7.7 |
| Second granule | MCC | 23 |
| | Povidone | 8 |
| Extragranular | Magnesium stearate | 2 |

Tablet friability was determined according to section 2.9.7 in the European Pharmacopoeia 7.5, 7th edition 2012 using tablets prepared at a main compression force of around 3 kN with granule product from test 2, test 3, and test 4 and the results are presented in table 6.1.

TABLE 6.1

Tablet friability

| Sieve setup | Replicate | Tablet friability (test 2) | Tablet friability (test 3) | Tablet friability (test 4) |
|---|---|---|---|---|
| Sieve with guide | 1 | 1.2% | 0.8% | 1.0% |
| Sieve with guide | 2 | 1.4% | 0.9% | 0.9% |
| Sieve with guide | 3 | 1.1% | 0.6% | 1.0% |
| Sieve with guide | Average | 1.2% | 0.8% | 1.0% |
| Sieve without guide | 1 | 1.7% | 1.5% | 1.6% |
| Sieve without guide | 2 | 1.6% | 1.8% | 1.2% |
| Sieve without guide | 3 | 1.6% | 1.5% | 1.2% |

TABLE 6.1-continued

Tablet friability

| Sieve setup | Replicate | Tablet friability (test 2) | Tablet friability (test 3) | Tablet friability (test 4) |
|---|---|---|---|---|
| Sieve without guide | Average | 1.6% | 1.6% | 1.3% |

The results show that the tablets prepared using the granule product obtained with the sieve guide have a significantly lower friability than tablets prepared using the granule product obtained without the sieve guide. Tablets prepared with granule products using a sieve with guide results therefore in tablets with a higher mechanical strength.

To further analyze the mechanical strength of the tablets prepared, the tablet resistance to crushing was evaluated. Resistance to crushing of tablets was determined according to section 2.9.8 in the European Pharmacopoeia 7.5, 7th edition 2012 using 20 tablets as sample size and a jaw speed of 1.2 mm/s and oriented so that the tablet failure occurred along the major axis of the tablet. The results are included in table 6.2.

TABLE 6.2

Tablet resistance to crushing

| Sieve setup | Main compression force | Tablet resistance to crushing (test 2) | Tablet resistance to crushing (test 3) | Tablet resistance to crushing (test 4) |
|---|---|---|---|---|
| Sieve with guide | 3 kN | 26N | 32N | 29N |
| Sieve with guide | 5 kN | 59N | 55N | 61N |
| Sieve with guide | 7-8 kN | 94N | 90N | 93N |
| Sieve with guide | 10-11 kN | 127N | 131N | 134N |
| Sieve with guide | 12-13 kN | 130N | 136N | 137N |
| Sieve with guide | 15 kN | 155N | 154N | 157N |
| Sieve without guide | 3 kN | 24N | 23N | 26N |
| Sieve without guide | 5 kN | 52N | 51N | 55N |
| Sieve without guide | 7-8 kN | 87N | 80N | 89N |
| Sieve without guide | 10-11 kN | 122N | 127N | 128N |
| Sieve without guide | 12-13 kN | 130N | 125N | 124N |
| Sieve without guide | 15 kN | 143N | 135N | 145N |

The results show that the tablets prepared using the granule product obtained with the sieve guide have a higher breaking force than tablets prepared using the granule product obtained without the sieve guide. Together with the results for the tablet friability this demonstrates that tablets obtained using granule products obtained with the sieve guide have an improved mechanical strength compared with tablets obtained using granule products obtained without the sieve guide.

The invention claimed is:

1. A sieve guide assembly a circular sieve screen and a sieve guide,
    wherein the sieve guide is fixedly attached to the circular sieve screen;
    wherein the circular sieve guide comprises:
       (a) a circular guide portion adapted to guide a central guided orbital flow, wherein the central guided orbital flow defines an orbital downstream direction,
       wherein the circular guide portion is positioned centrally on the circular sieve screen and defines a central loading area of the sieve screen,
       wherein the circular guide portion comprises a first radial opening extending in an upstream orbital direction from a first to a second side, and
       wherein the upstream orbital direction is opposite a downstream orbital direction, and
       (b) a lateral guide portion adapted to guide a lateral guided flow of granules from the central loading area of the sieve screen,
       wherein the lateral guide portion comprises a first lateral guide member extending in a lateral direction from the first side of the first radial opening and to a periphery of the sieve screen;
    wherein the sieve guide assembly is adapted to be mounted in a fractionating device in a specific angular position with the first lateral guide member aligned with a first side of an outlet of the fractionating device; and
    wherein when the sieve guide assembly is mounted in the specific angular position in the fractionating device and when the fractionating device induces an orbital and a lateral flow, the lateral guided flow of the granules is guided along the first lateral guide member to the outlet.

2. The sieve guide assembly according to claim 1, wherein the first lateral guide member is curved.

3. The sieve guide assembly according to claim 1, further comprising a second lateral guide member extending in the lateral direction from the second side of the first radial opening.

4. The sieve guide assembly according to claim 3, wherein the second lateral guide member is curved.

5. The sieve guide assembly according to claim 1, wherein the sieve guide assembly comprises a key or a key-hole adapted to ensure the sieve guide assembly is mounted in the specific angular position.

6. The sieve guide assembly according to claim 1, wherein the sieve guide assembly is adapted to be angularly adjustable, and wherein the sieve guide further is adapted to be fixed or clamped at the specific angular position.

7. A sieve guide assembly, comprising:
    a circular sieve screen and a sieve guide;
    wherein the sieve guide is fixedly attached to the sieve screen,
    wherein the sieve guide comprises:
       (a) a circular guide portion comprising a first radial opening extending from a first to a second side wherein the circular portion is positioned centrally on the circular sieve screen and defines a central loading area of the sieve screen for granules to be fractionated,
       (b) a lateral guide portion comprising (i) a first lateral guide member extending from a first side of the first radial opening to a periphery of the sieve screen, and (ii) a second lateral guide member extending from a second side of the first radial opening towards the periphery;
    wherein when the sieve guide assembly is mounted in a fractionating device and when the fractionating device induces an orbital and a lateral flow, the lateral guided flow of the granules are guided along the first and second lateral guide members.

8. A fractionating device adapted to fractionate granules for solid dosage forms, comprising: (a) the sieve guide assembly according to claim 1 or claim 7, and (b) a tubular rim portion adapted to receive the sieve guide assembly,
  wherein the tubular rim portion comprises an outlet;
  wherein the outlet comprises an opening in the tubular rim portion extending in the upstream orbital direction from a first to a second side.

9. A fractionating device adapted to fractionate granules, comprising:
  (a) a sieve deck comprising an inlet and a tubular rim portion comprising an outlet, wherein the outlet comprises an opening extending from a first to a second side, and
  (b) a sieve screen and a sieve guide received in the sieve deck, wherein the sieve guide is fixedly attached to the sieve screen;
  wherein the sieve guide comprises:
    (i) a circular guide portion comprising a first radial opening extending from a first to a second side, wherein the circular guide portion is positioned centrally on the sieve screen and defines a central loading area of the sieve screen adapted to receive granules through the inlet, and
    (ii) a lateral guide portion comprising a first guide member extending from the first side of the first radial opening to a periphery of the sieve screen;
  wherein the outlet of the sieve deck comprises an opening extending from a first to a second side;
  wherein the sieve guide is arranged in a specific angular position with the first lateral guide member aligned with the first side of the outlet of the sieve deck;
  wherein the first radial opening is arranged with an angular overlap with the outlet; and
  wherein when the fractionating device induces an orbital and a lateral flow, the granules are guided along the first lateral guide member to the outlet.

10. The fractionating device according to claim 9, wherein the first lateral guide member is curved.

11. The fractionating device according to claim 9, further comprising a second lateral guide member extending in the lateral direction from the second side of the first radial opening.

12. A method of fractionating granules for solid dosage forms comprising;
  a) loading the granules to be fractionated onto the central loading area of the screen of the fractionating device according to claim 8,
  b) fractionating the granules; and
  c) collecting the fractionated granules at the outlet.

13. A method of producing a solid dosage form comprising;
  a) obtaining granules comprising a salt of N-(8-(2-hydroxybenzoyl) amino) caprylic acid (NAC);
  b) fractionating the granules using the fractionation device according to claim 8 and
  c) preparing the solid dosage form using the fractionated granules.

14. The method according to claim 13, wherein the solid dosage form comprises one or more pharmaceutical active ingredients and optionally one or more pharmaceutically acceptable excipients.

15. The fractionating device according to claim 11, wherein the second lateral guide member is curved.

16. The method according to claim 12, wherein the solid dosage form is selected from the group consisting of a tablet, capsule, and sachet.

17. The method according to claim 13, wherein the solid dosage form is selected from the group consisting of a tablet, capsule, and sachet.

18. The method according to claim 14, wherein the solid dosage form is selected from the group consisting of a tablet, capsule, and sachet.

* * * * *